US010885342B1

(12) United States Patent
Day

(10) Patent No.: US 10,885,342 B1
(45) Date of Patent: Jan. 5, 2021

(54) INTELLIGENT MONITORING CAMERA USING COMPUTER VISION AND INTELLIGENT PERSONAL AUDIO ASSISTANT CAPABILITIES TO MAINTAIN PRIVACY

(71) Applicant: Ambarella International LP, Santa Clara, CA (US)

(72) Inventor: Christopher N. Day, Los Gatos, CA (US)

(73) Assignee: Ambarella International LP, Santa Clara, CO (US)

( * ) Notice: Subject to any disclaimer, the term of this patent is extended or adjusted under 35 U.S.C. 154(b) by 44 days.

(21) Appl. No.: 16/207,542

(22) Filed: Dec. 3, 2018

(51) Int. Cl.
| H04N 7/18 | (2006.01) |
| G06K 9/00 | (2006.01) |
| A61B 5/00 | (2006.01) |
| G08B 21/04 | (2006.01) |
| G10L 15/07 | (2013.01) |
| G10L 15/08 | (2006.01) |

(52) U.S. Cl.
CPC ........ *G06K 9/00718* (2013.01); *A61B 5/0022* (2013.01); *G06K 9/00771* (2013.01); *G08B 21/043* (2013.01); *G08B 21/0423* (2013.01); *G10L 15/07* (2013.01); *G10L 15/08* (2013.01); *G06K 2009/00738* (2013.01); *G10L 2015/088* (2013.01)

(58) Field of Classification Search
CPC ...................... G06K 9/00718; G06K 9/00771
See application file for complete search history.

(56) References Cited

U.S. PATENT DOCUMENTS

| 2010/0057840 | A1* | 3/2010 | Schlusser .......... H04L 29/08846 709/203 |
| 2016/0232890 | A1* | 8/2016 | Pfalzgraf ................. G10L 15/30 |
| 2017/0076571 | A1* | 3/2017 | Borel ............... G08B 13/19673 |
| 2017/0223314 | A1* | 8/2017 | Collings, III ........ H04N 5/2259 |
| 2018/0025498 | A1* | 1/2018 | Omari ................ G06K 9/00711 348/144 |
| 2019/0141297 | A1* | 5/2019 | Vaidya .................... H04N 5/772 |
| 2020/0058309 | A1* | 2/2020 | Lee ......................... G10L 17/02 |

OTHER PUBLICATIONS

Moren, "Alexa vs Google Assistant vs Siri: Google Widens Its Lead", https://www.tomsguide.com/us/alexa-vs-siri-vs-google,review-4772.html, Jun. 4, 2018, pp. 1-13.

* cited by examiner

*Primary Examiner* — Fabio S Lima
(74) *Attorney, Agent, or Firm* — Christopher P. Maiorana, PC

(57) ABSTRACT

An apparatus includes a video capture device, an audio capture device and a processor. The video capture device may be configured to generate a plurality of video frames. The audio capture device may be configured to capture audio. The processor may be configured to perform video operations to detect objects in the video frames, extract data about the objects based on characteristics of the objects determined using the video operations, detect whether an event has occurred based on the characteristics of the objects, determine a permission status based on the captured audio and generate a video stream based on the video frames. The video stream may be generated only if the permission status allows the video stream. The captured audio may be monitored after the event has been detected to determine whether the permission status allows the video stream.

17 Claims, 12 Drawing Sheets

INTELLIGENT MONITORING CAMERA USING COMPUTER VISION AND INTELLIGENT PERSONAL AUDIO ASSISTANT CAPABILITIES TO MAINTAIN PRIVACY

FIELD OF THE INVENTION

The invention relates to video capture generally and, more particularly, to a method and/or apparatus for intelligent monitoring camera using computer vision and intelligent personal audio assistant capabilities to maintain privacy.

BACKGROUND

Home monitoring cameras with an integrated intelligent personal audio assistant are becoming more popular. The integrated intelligent personal audio assistant has the capability of allowing user instructions to be interpreted via verbal commands. Remote monitoring is an efficient and convenient way to check a status of a remote location. However, as cameras are becoming ubiquitous, privacy is becoming more and more of a concern. Constant video monitoring can be a significant invasion of privacy, especially in the home or in medical situations. For example, while remotely monitoring elderly people or medical patients can be beneficial to ensure safety and well being, there is a trade-off with privacy because continuous streaming of video creates a privacy issue for the patient. Furthermore, the person being monitored may not be able to use applications that control the camera either because of physical disability, a technical incompetency and/or because the person being monitored does not have physical access to a device that controls the camera such as a smartphone or tablet.

It would be desirable to implement an intelligent monitoring camera using computer vision and intelligent personal audio assistant capabilities to maintain privacy.

SUMMARY

The invention concerns an apparatus comprising a video capture device, an audio capture device and a processor. The video capture device may be configured to generate a plurality of video frames. The audio capture device may be configured to capture audio. The processor may be configured to perform video operations to detect objects in the video frames, extract data about the objects based on characteristics of the objects determined using the video operations, detect whether an event has occurred based on the characteristics of the objects, determine a permission status based on the captured audio and generate a video stream based on the video frames. The video stream may be generated only if the permission status allows the video stream. The captured audio may be monitored after the event has been detected to determine whether the permission status allows the video stream.

BRIEF DESCRIPTION OF THE FIGURES

Embodiments of the invention will be apparent from the following detailed description and the appended claims and drawings in which:

DETAILED DESCRIPTION OF THE EMBODIMENTS

Embodiments of the present invention include providing an intelligent monitoring camera using computer vision and intelligent personal audio assistant capabilities to maintain privacy that may (i) enable remote video monitoring, (ii) provide privacy for a person being monitored, (iii) perform computer vision operations to detect events, (iv) enable a person being monitored to control when video is streamed, (v) convert detected events to text and/or (vi) be implemented as one or more integrated circuits.

Figure 1:
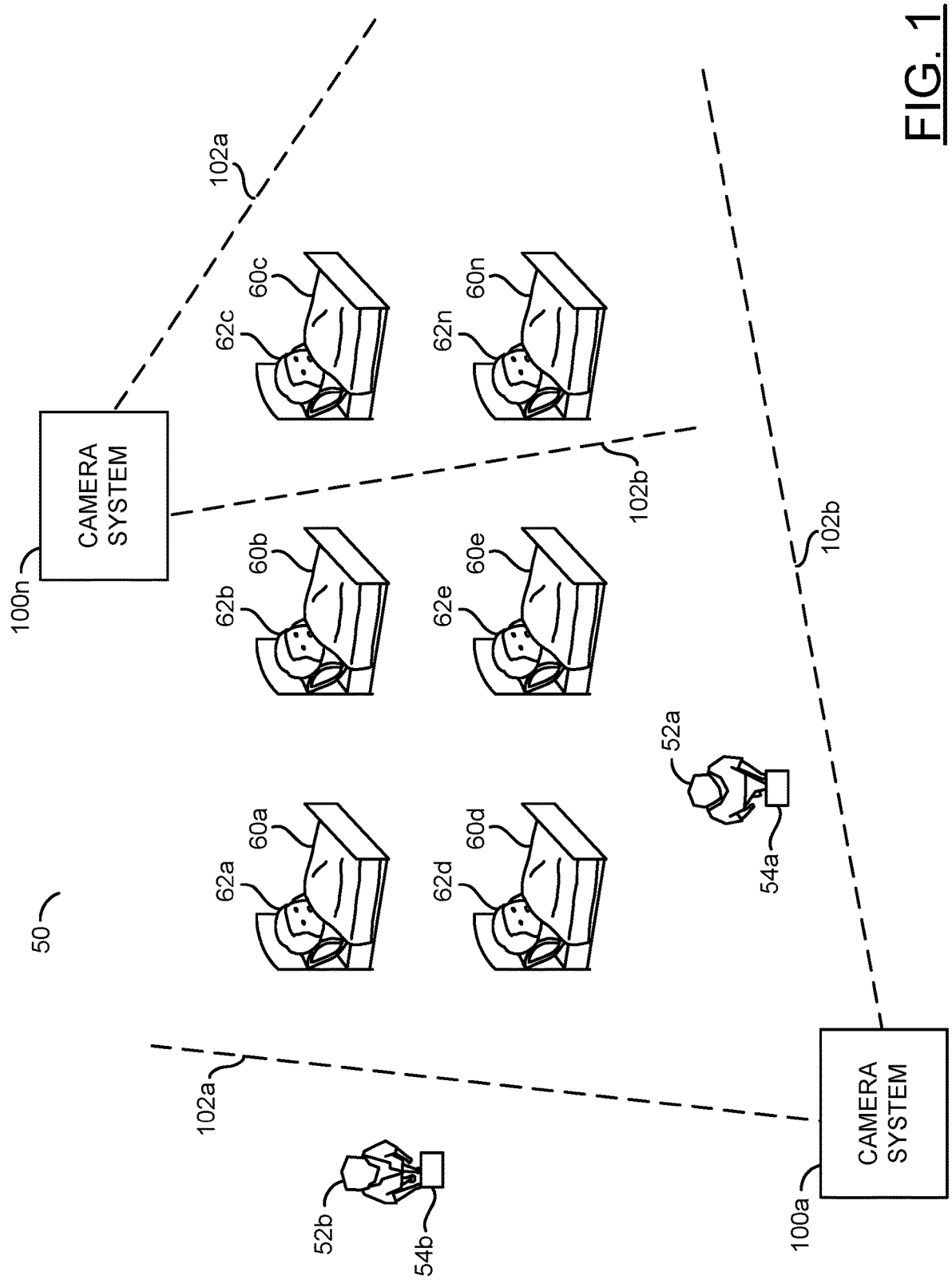
FIG. 1 is a diagram illustrating an example embodiment of the invention.

Referring to FIG. 1, a diagram illustrating an example embodiment of the invention is shown. An example scenario 50 is shown. The example scenario 50 may comprise a number of people 52a-52b, a number of remote devices 54a-54b, a number of objects 60a-60n, a number of people 62a-62n and/or a number of apparatuses (or blocks, or circuits, or devices) 100a-100n. The devices 100a-100n may each be configured to implement an embodiment of the present invention. The devices 100a-100n may each implement a camera system featuring an intelligent personal audio assistant.

The camera systems 100a-100n may be configured to capture video and/or audio. The camera systems 100a-100n may be configured to interpret instructions and/or responses from the received audio. In an example, a person may talk to one or more of the camera systems 100a-100n to provide audio instructions (e.g., give permission to begin video streaming and/or deny permissions in order to stop video streaming). The camera systems 100a-100n may interpret the instructions and/or perform commands (e.g., features, functions, responses, etc.). In some embodiments, the camera systems 100a-100n may be connected (e.g., wireless, wired, etc.) to other devices such as the remote devices 54a-54b. In one example, the camera systems 100a-100n may receive permission to initiate video streaming and the camera systems 100a-100n that have permission may stream video to one or more of the remote devices 54a-54b. In another example, the camera systems 100a-100n may perform responses to the audio instructions by accessing other devices (e.g., provide a signal to an actuator to cause the actuator to perform the desired command). In some embodiments, the camera systems 100a-100n may be configured to perform a command in response to the spoken instructions by using internal components of the camera systems 100a-100n. The types of commands performed and/or how the apparatuses 100a-100n perform the commands may be varied according to the design criteria of a particular implementation.

The camera system 100a and the camera system 100n are shown in the example scenario 50 as representative examples of the camera systems 100a-100n. Lines 102a-102b are shown extending from the camera system 100a and the camera system 100n. The lines 102a-102b may represent a field of view of the camera system 100a and the camera system 100n. The camera system 100a and the camera system 100n may capture video frames of the area within the respective fields of view 102a-102b. In the example scenario 50, the lines 102a-102b may provide an illustrative example of the field of view of the camera system 100a and/or the camera system 100n. In some embodiments, the camera systems 100a-100n may comprise one single 360-degree camera (e.g., capturing a 360-degree field of view). In some embodiments, the camera systems 100a-100n may comprise two back-to-back 180-degree cameras for capturing two 180-degree fields of view (e.g., in front and behind the camera systems 100a-100n). In some embodiments, the camera systems 100a-100n may implement a fisheye lens providing a wide-angle field of view. The types of lenses used and/or the field of view captured by the camera systems 100a-100n may be varied according to the design criteria of a particular implementation.

Sounds may be captured by the camera systems 100a-100n. The sound captured by the camera systems 100a-100n may be analyzed to determine a permission status for video streaming. In one example, if permission for video streaming is not provided, the camera systems 100a-100n may not stream video data to the remote devices 54a-54b. In another example, if permission for video streaming is provided, the camera systems 100a-100n may stream the video data to the remote devices 54a-54b. Audio processing may be implemented by the camera systems 100a-100n in order to parse speech commands from the captured audio (e.g., the captured audio may comprise white noise, ambient noise, background noise, voices of other speakers, voices of the people 52a-52b, voices of the people 62a-62n, etc.). The speech commands may be analyzed by the camera systems 100a-100n in order to determine the permission status.

In the example scenario 50, the people 52a-52b may be subject monitors (e.g., doctors, nurses, patient monitors). The patient monitors 52a-52b are shown holding the remote devices 54a-54b. The camera systems 100a-100n may be configured to stream video to the remote devices 54a-54b when permission is provided by people (e.g., subjects) being monitored.

In the example scenario 50, the people 62a-62n (e.g., subjects) are each shown lying in a respective one of the beds 60a-60n. In one example, the people 62a-62n may be patients lying in the hospital beds 60a-60n. For example, in the example scenario 50, the camera system 100a and the camera system 100n may be configured to monitor the patients 62a-62n (e.g., in a hospital, in a rest home, in a drug rehabilitation center, etc.). For example, the camera system 100a may monitor one portion of the patients (e.g., the patients 62a, 62b, 62d and 62e) and the camera system 100n may monitor another portion of the patients (e.g., the patients 62c and 62n). The patients 62a-62n may be the subjects of the video monitoring. For example, the camera systems 100a-100n may determine the identity of a person speaking (e.g., using facial recognition operations to determine whether the person is the subject of the video monitoring) and then determine whether the subject of the video monitoring has provided permission to stream video. The camera systems 100a-100n may need to receive permission from the patients 62a-62n before video streaming to the remote devices 54a-54b is enabled.

In the example scenario 50, the person 52a may be within the field of view 102a-102b of the camera system 100a and outside of the field of view 102a-102b of the camera system 100n. The person 52b may be outside of the field of view 102a-102b of the camera system 100a and the camera system 100n. In the example shown, the person 52b may not be visible in the video frames captured by the camera systems 100a-100n. Sound from the person 52b may be captured by the camera systems 100a-100n. In some embodiments, the camera systems 100a-100n may not need to receive permission from patient monitors 52a-52b to stream video (e.g., the patient monitors 52a-52b may appear in the video frames but are not the subject of the monitoring). In some embodiments, any person that appears in the captured video frames (e.g., the patient monitors 52a-52b and/or the patients 62a-62n) may need to provide permission before the video data may be streamed.

The video monitoring camera systems 100a-100n may be used to monitor the subjects 62a-62n and use computer vision-based video analytics to extract data from the captured video. The data extracted from the captured video may be used to provide information to the patient monitors 52a-52b, without streaming the video content. By providing information without video streaming, the camera systems 100a-100n may provide a level of privacy for the patients 62a-62n.

The camera systems 100a-100n may be configured to detect characteristics of each of the subjects 62a-62n by using the computer vision operations. The characteristics of the subjects 62a-62n may be based on a movement, a sequence of movements, a lack of movement, an orientation of the body and/or body parts, a position of the body and/or body parts with respect to another object (e.g., lying in bed), etc. The characteristics of the subjects 62a-62n may be used by the camera systems 100a-100n to determine whether an event has occurred. The event may be a circumstance that may need the intervention of the monitors 52a-52b. In one example, one of the events may be the camera systems 100a-100n detecting that the patient has not moving for a period of time. In another example, one of the events may be the camera systems 100a-100n detecting that the patient is lying down in an area other than the bed (e.g., fallen out of bed). In still another example, one of the events may be the camera system 100a-100n detecting that the patient has left a particular area (or entered a restricted area). The types of characteristics and/or events detected by the camera systems 100a-100n may be varied according to the design criteria of a particular implementation.

Once an event has been detected, the camera systems 100a-100n may automatically initiate a voice message to attempt to communicate with the subjects(s) 62a-62n. In one example, the voice message may ask the subjects(s) 62a-62n if they are hurt or need assistance. The camera systems 100a-100n may be configured to monitor for a response from the subjects(s) 62a-62n and/or analyze the response. Based on the analysis of the response (or a lack thereof), the camera systems 100a-100n may send an alarm and/or message to one or more of the monitors 52a-52n (e.g., to the remote devices 54a-54b). In some embodiments, the camera systems 100a-100n may employ multiple wide angle fields of view to provide full surveillance coverage over a wide area and/or multiple rooms.

The camera systems 100a-100n may be controlled by voice commands from the subjects 62a-62n using integrated personal intelligent audio assistant technology. In one example, one of the patients 62a-62n may initiate a request for help directly by verbally addressing one or more of the camera systems 100a-100n. In some embodiments, the patients 62a-62n may give permission to turn video streaming on or off. In some embodiments, the camera systems 100a-100n may be configured to implement a 2-way audio capability (e.g., between one of the camera systems 100a-100n and one or more of the remote devices 54a-54b). For example, if an alert is triggered by the video analytics data (e.g., an event is detected), the remote devices 54a-54b may present a notification to the remote devices 54a-54b. The patient monitors 52a-52b may respond to the notification using the remote devices 54a-54b (e.g., using the 2-way audio capability). For example, the patient monitors 52a-52b may first verbally ask the patient if it is okay to turn on video streaming. The camera systems 100a-100n may only turn on the video streaming permission to stream is received from the patient(s) 62a-62n (or if no response is forthcoming from the patient).

Figure 2:
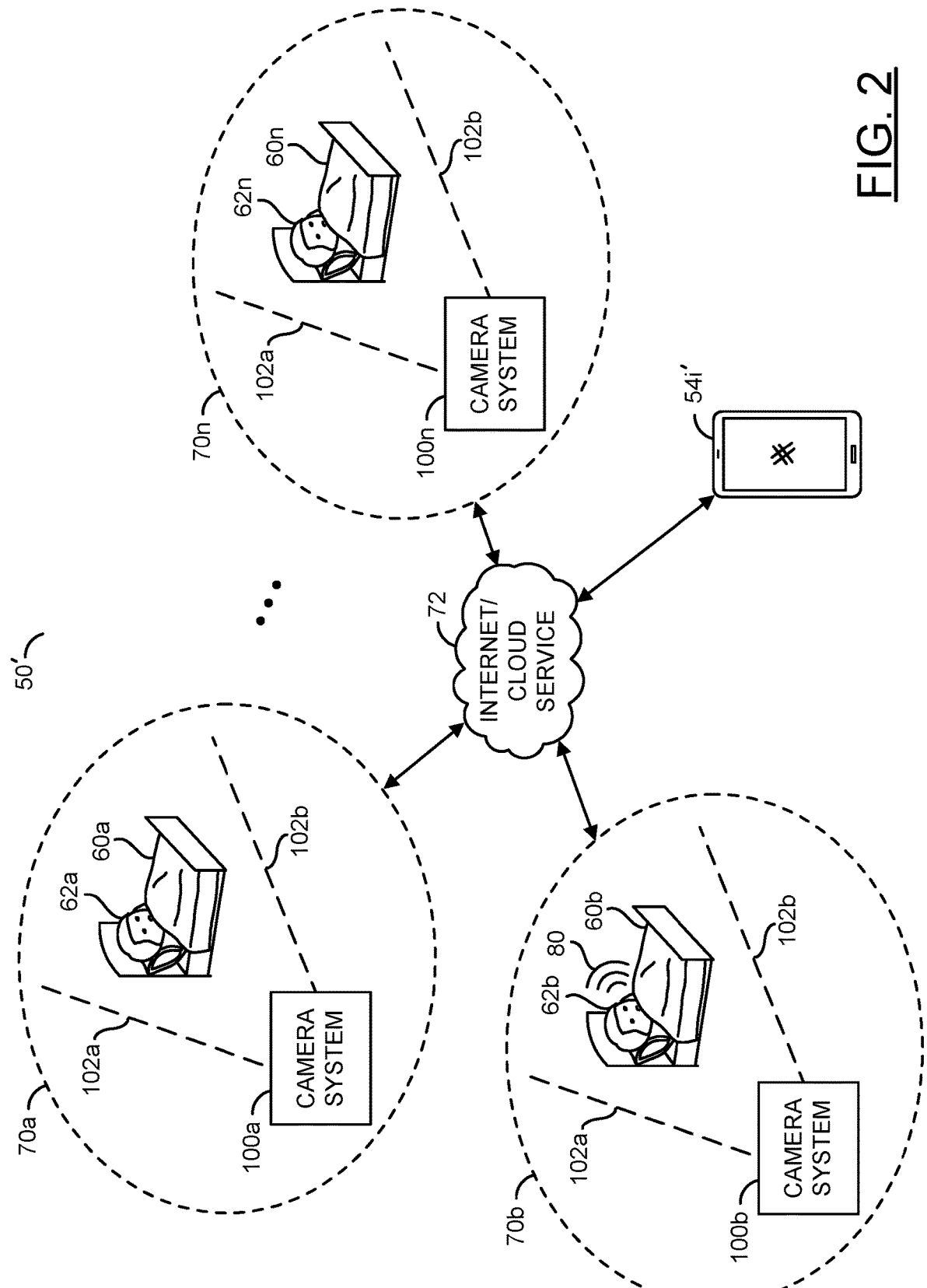
FIG. 2 is a diagram illustrating an alternate example embodiment of the invention.

Referring to FIG. 2, a diagram illustrating an alternate example embodiment of the invention is shown. An alternate example scenario 50' is shown. The alternate example scenario 50' may comprise the remote device 54i', a number of locations 70a-70n, and/or a network 72. In some embodiments, the locations 70a-70n may be remote locations (e.g., different geographic locations such as different cities, different countries, different areas within the same city, etc.). In some embodiments, the locations 70a-70n may be different locations within the same building (e.g., different hospital rooms, different hotel rooms, different cubicles in an office, etc.).

The remote device 54i' may have an implementation similar to the remote devices 54a-54b shown in association with FIG. 1. In the example shown, the remote device 54i' may be implemented as a smartphone. In another example, the remote device 54i' may be implemented as a tablet computing device, a desktop computer, a phablet, a wearable headset, a patient monitor, etc. Generally, the remote device 54i' may comprise a display, a speaker, a microphone and/or a user input device. The remote device 54i' may be configured to display the video stream from the camera systems 100a-100n. The remote device 54i' may be configured to receive audio from the camera systems 100a-100n and/or send audio to the camera systems 100a-100n (e.g., implement 2-way audio communication). In the example shown, one remote device 54i' is shown. However, the example scenario 50' may be implemented having multiple remote devices (e.g., remote devices 54a'-54n'). In the example shown, the remote device 54i' is shown at a location other than the locations 70a-70n. For example, streaming the video data may enable monitoring of a person from a remote geographic location. In some embodiments, the remote device 54i' may be located at or near one of the locations 70a-70n. In some embodiments, the remote device 54i' may be at a remote geographic location.

The network 72 may be a wide area network (e.g., the internet) and/or a local area network. The network 72 may enable communication between the camera systems 100a-100n and/or the remote device 54i'. The network 72 may implement wired communication, wireless communication and/or a combination of wired communication and wireless communication. The network 72 may comprise a number of server computers. The network 72 may be configured to store data, retrieve and transmit stored data, process data and/or communicate with other devices. The network 72 may be implemented as part of a cloud computing platform (e.g., distributed computing). In an example, the network 72 may be implemented as a group of cloud-based, scalable server computers. By implementing a number of scalable servers, additional resources (e.g., power, processing capability, memory, etc.) may be available to process and/or store variable amounts of data. For example, the network 72 may be configured to scale (e.g., provision resources) based on demand. The network 72 may implement scalable computing (e.g., cloud computing). The scalable computing may be available as a service to allow access to processing and/or storage resources without having to build infrastructure. In some embodiments, the network 72 may be configured to provide scalable resources for transmitting video data, performing computer vision operations and/or for analyzing audio data.

The locations 70a-70n may each comprise a respective one of the beds 60a-60n, a respective one of the patients 62a-62n and/or a respective one of the camera systems 100a-100n. Each of the cameras 100a-100n are shown having the field of view 102a-102b. In the example shown, the patients 62a-62n may be the subject of the monitoring.

In some embodiments, one camera system 100a may monitor multiple subjects (e.g., a hospital environment where many patients might be in a single ward as shown in association with FIG. 1). In some embodiments, each of the camera systems 100a-100n may monitor a single subject. In one example, the camera systems 100a-100n may be configured to monitor a patient (or patients) remotely. For example, the locations 70a-70n may be the homes of the patients 62a-62n. Generally, having each of the subjects 62a-62n alone at a separate one of the location 70a-70n may offer a high amount of privacy. In the example shown, the remote device 54i' may be at a separate location from the locations 70a-70n and communicate to the network 72 using cellular communication.

Audio 80 is shown in the location 70b. The audio 80 may represent speech (e.g., a voice/verbal command, a response, talking, a keyword, etc.) by the patient 62b. In one example, the audio 80 may be a response by the patient 62b to an audio output from the camera system 100b (e.g., the camera system 100b may output audio asking if the patient 62b is willing to give permission to stream video and the audio 80 may be the user granting or denying permission). In another example, the audio 80 may be the patient 62b rescinding a previously granted permission to stream (e.g., the patient 62b may have given permission to stream the video but later wants to stop video streaming). In yet another example, the audio 80 may be a keyword spoken by the patient 62b that may enable the camera system 100b to accept a voice command. The type of audio 80 spoken by the patient 62b may be varied according to the design criteria of a particular implementation.

The intelligent audio features of the camera systems 100a-100n may be configured to capture the audio 80 and/or analyze the audio 80. The subject 62b may be within the field of view 102a-102b of the camera system 100b. The sound 80 from the subject 62b may be captured by the camera system 100b. In the example shown, the subject 62b may be providing the speech command 80 to the camera system 100b. The subject 62b may be the speaker (e.g., an audio source).

The camera systems 100a-100n may be configured to locate the source (e.g., the subject 62b) of the audio 80. The camera systems 100a-100n may each implement a directional microphone arrangement. The directional microphone arrangement may be configured to receive the audio commands 80. The directional microphone arrangement of the camera systems 100a-100n may be configured to identify (e.g., locate, triangulate, etc.) the direction of the user/speaker (e.g., the source of the audio 80).

The camera systems 100a-100n may be configured to distinguish between the audio command (or response) 80 by the subject 62b and other audio in the environment (e.g., other people talking, ambient noise, etc.). In one example, the audio 80 may start with a particular keyword. Once the keyword is detected, the camera system 100b may interpret the following captured audio as the audio command 80. In some embodiments, the camera systems 100a-100n may implement speech detection to extract the audio 80 from audio in the environment. The method of detecting the audio 80 may be varied according to the design criteria of a particular implementation.

The camera system 100b may be configured to capture video data of the field of view 102a-102n at the location 70b. In one example, if the camera system 100b detects the audio 80, the camera system 100b may determine the audio command and/or determine whether the subject 62b has granted permission to stream video. In another example, if the camera system 100b detects an event in the video data, the camera system 100b may playback an audio message to ask the subject 62b for permission to stream the video data. If the audio 80 grants permission to stream, the camera system 100b may stream the captured video to the remote device 54i' via the network 72. If the audio 80 denies permission to stream, the camera system 100b may not stream the video. Instead of streaming the video, the camera system 100b may analyze the video data and convert the detected event to a human readable format (e.g., text, a symbol, etc.) and communicate the converted data to the remote device 54i'.

Figure 3:
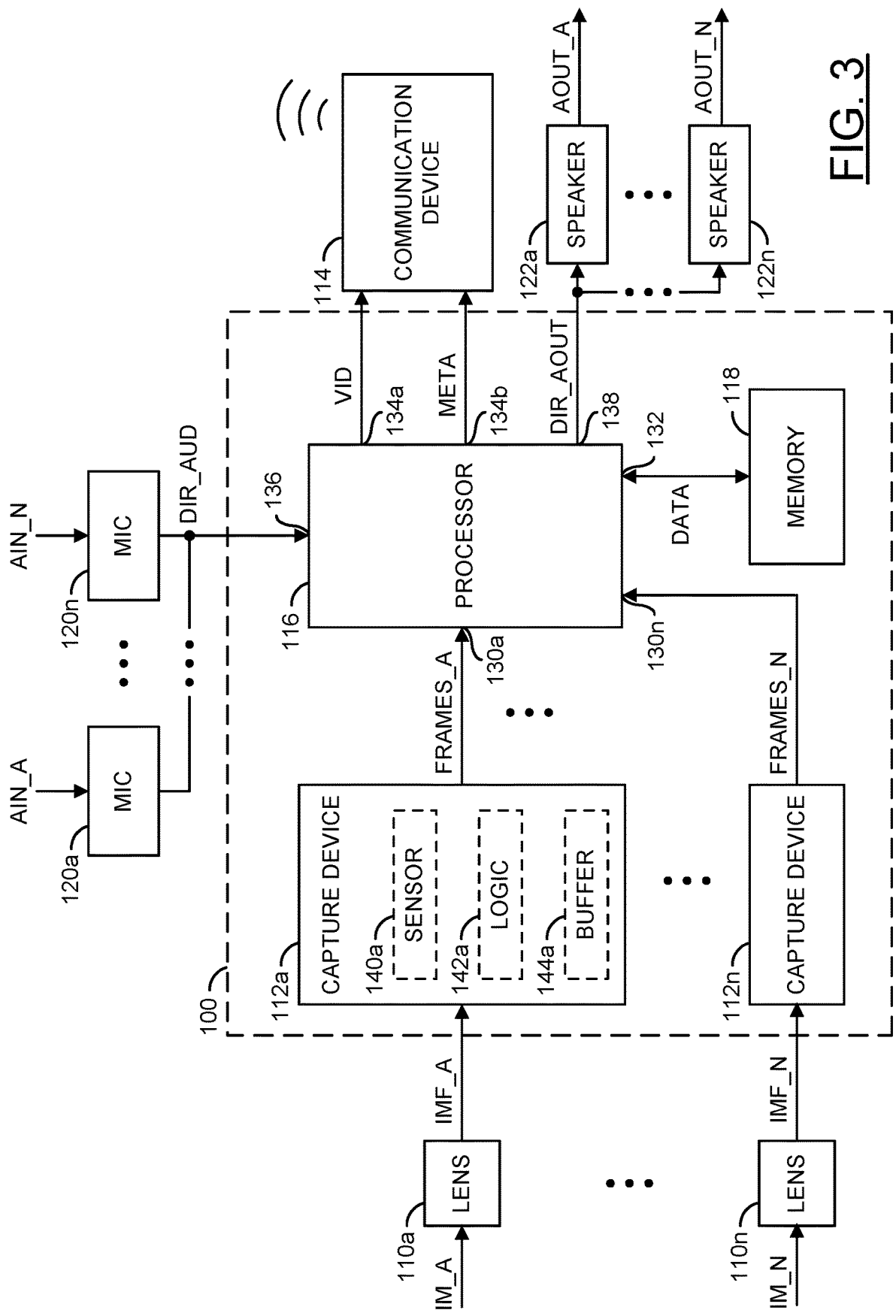
FIG. 3 is a block diagram illustrating an example embodiment of the invention.

Referring to FIG. 3, a block diagram illustrating an example embodiment of the invention is shown. The apparatus 100 is shown. The apparatus 100 may be a representative example of the camera system 100a-100n shown in association with FIG. 1 and FIG. 2. The apparatus 100 generally comprises blocks (or circuits) 110a-110n, blocks (or circuits) 112a-112n, a block (or circuit) 114, a block (or circuit) 116, a block (or circuit) 118, blocks (or circuits) 120a-120n and/or blocks (or circuits) 122a-122n. The blocks 110a-110n may implement lenses. The circuits 112a-112n may implement capture devices. The circuit 114 may implement a communication device. The circuit 116 may implement a processor. The circuit 118 may implement a memory. The circuits 120a-120n may implement microphones (e.g., audio capture devices). The circuits 122a-122n may implement audio output devices (e.g., speakers). The apparatus 100 may comprise other components (not shown). The number, type and/or arrangement of the components of the apparatus 100 may be varied according to the design criteria of a particular implementation.

In an example implementation, the circuit 116 may be implemented as a video processor. The processor 116 may comprise inputs 130a-130n and/or other inputs. The processor 116 may comprise an input/output 132. The processor 116 may comprise outputs 134a-134b. The processor 116 may comprise an input 136. The processor 116 may comprise an output 138 and/or other outputs. The number of inputs, outputs and/or bi-directional ports implemented by the processor 116 may be varied according to the design criteria of a particular implementation.

In the embodiment shown, the capture devices 112a-112n may be components of the apparatus 100. In some embodiments, the capture devices 112a-112n may be separate devices (e.g., remotely connected to the camera system 100, such as a drone, a robot and/or a system of security cameras configured to send captured video data to a central location) configured to send data to the apparatus 100. In one example, the capture devices 112a-112n may be implemented as part of an autonomous robot configured to patrol particular paths such as hallways. Similarly, in the example shown, the wireless communication device 114, the microphones 120a-120n and/or the speakers 122a-122n are shown external to the apparatus 100 but in some embodiments may be a component of the apparatus 100.

The apparatus 100 may receive one or more signals (e.g., IMF_A-IMF_N) and/or one or more signals (e.g., DIR_AUD). The apparatus 100 may present a signal (e.g., VID), a signal (e.g., META) and/or a signal (e.g., DIR_AOUT). The capture devices 112a-112n may receive the signals IMF_A-IMF_N from the corresponding lenses 110a-110n. The processor 116 may receive the signal DIR_AUD from the microphones 120a-120n. The processor 116 may present the signal VID and the signal META to the communication device 114. For example, the wireless communication device 114 may be a radio-frequency (RF) transmitter. In another example, the communication device 114 may be a Wi-Fi module. In another example, the communication device 114 may be a device capable of implementing RF transmission, Wi-Fi, Bluetooth and/or other wireless communication protocols. The processor 116 may present the signal DIR_AOUT to the speakers 122a-122n.

The lenses 110a-110n may capture signals (e.g., IM_A-IM_N). The signals IM_A-IM_N may be an image (e.g., an analog image) of the environment near the camera system 100 that are presented by the lenses 110a-110n to the capture devices 112a-112n as the signals IMF_A-IMF_N. The lenses 110a-110n may be implemented as an optical lens. The lenses 110a-110n may provide a zooming feature and/or a focusing feature. The capture devices 112a-112n and/or the lenses 110a-110n may be implemented, in one example, as a single lens assembly. In another example, the lenses 110a-110n may be a separate implementation from the capture devices 112a-112n. The capture devices 112a-112n are shown within the circuit 100. In an example implementation, the capture devices 112a-112n may be implemented outside of the circuit 100 (e.g., along with the lenses 110a-110n as part of a lens/capture device assembly).

The capture devices 112a-112n may be configured to capture image data for video (e.g., the signals IMF_A-IMF_N from the lenses 110a-110n). In some embodiments, the capture devices 112a-112n may be video capturing devices such as cameras. The capture devices 112a-112n may capture data received through the lenses 110a-110n to generate bitstreams (e.g., generate video frames). For example, the capture devices 112a-112n may receive focused light from the lenses 110a-110n. The lenses 110a-110n may be directed, tilted, panned, zoomed and/or rotated to provide a targeted view from the camera system 100 (e.g., to provide coverage for a panoramic field of view such as the field of view 102a-102b). The capture devices 112a-112n may generate signals (e.g., FRAMES_A-FRAMES_N). The signals FRAMES_A-FRAMES_N may be video data (e.g., a sequence of video frames). The signals FRAMES_A-FRAMES_N may be presented to the inputs 130a-130n of the processor 116.

The capture devices 112a-112n may transform the received focused light signals IMF_A-IMF_N into digital data (e.g., bitstreams). In some embodiments, the capture devices 112a-112n may perform an analog to digital conversion. For example, the capture devices 112a-112n may perform a photoelectric conversion of the focused light received by the lenses 110a-110n. The capture devices 112a-112n may transform the bitstreams into video data, video files and/or video frames. In some embodiments, the video data generated by the capture devices 112a-112n may be uncompressed and/or raw data generated in response to the focused light from the lenses 110a-110n. In some embodiments, the video data may be digital video signals. The video signals may comprise video frames.

In some embodiments, the video data may be encoded at a high bitrate. For example, the signal may be generated using a lossless compression and/or with a low amount of lossiness. The apparatus 100 may encode the video data captured by the capture devices 112a-112n to generate the signal COMM.

The communication device 114 may send and/or receive data to/from the apparatus 100. In some embodiments, the communication device 114 may be implemented as a wireless communications module. In some embodiments, the communication device 114 may be implemented as a satellite connection to a proprietary system. In one example, the communication device 114 may be a hard-wired data port (e.g., a USB port, a mini-USB port, a USB-C connector, HDMI port, an Ethernet port, a DisplayPort interface, a Lightning port, etc.). In another example, the communication device 114 may be a wireless data interface (e.g., Wi-Fi, Bluetooth, ZigBee, cellular, etc.).

The processor 116 may receive the signals FRAMES_A-FRAMES N from the capture devices 112a-112n at the inputs 130a-130n. The processor 116 may send/receive a signal (e.g., DATA) to/from the memory 118 at the input/output 132. The processor 116 may send a signal (e.g., VID) and/or a signal (e.g., META) to the communication device 114. The processor 116 may receive the signal DIR_AUD from the microphones 120a-120n. The processor 116 may send the signal DIR_AOUT to the speakers 122a-122n. In an example, the processor 116 may be connected through a bi-directional interface (or connection) to the capture devices 112a-112n, the communication device 114, the memory 118, the microphones 120a-120n and/or the speakers 122a-122n. The processor 116 may store and/or retrieve data from the memory 118. The memory 118 may be configured to store computer readable/executable instructions (or firmware). The instructions, when executed by the processor 116, may perform a number of steps.

The signal FRAMES_A-FRAMES_N may comprise video data (e.g., one or more video frames) providing a field of view captured by the lenses 110a-110n. The processor 116 may be configured to generate the signal VID, the signal META, the signal DIR_AOUT and/or other signals (not shown). The signal VID, the signal META and/or the signal DIR_AOUT may each be generated based on one or more decisions made and/or functions performed by the processor 116. The decisions made and/or functions performed by the processor 116 may be determined based on data received by the processor 116 at the inputs 130a-130n (e.g., the signals FRAMES_A-FRAMES_N), the input 132, the input 136 and/or other inputs.

The inputs 130a-130n, the input/output 132, the outputs 134a-134b, the input 136, the output 138 and/or other inputs/outputs may implement an interface. The interface may be implemented to transfer data to/from the processor 116, the communication device 114, the capture devices 112a-112n, the memory 118, the microphones 120a-120n, the speakers 122a-122n and/or other components of the apparatus 100. In one example, the interface may be configured to receive (e.g., via the inputs 130a-130n) the video streams FRAMES_A-FRAMES_N each from a respective one of the capture devices 112a-112n. In another example, the interface may be configured to receive (e.g., via the input 136) the directional audio DIR_AUD. In yet another example, the interface may be configured to transmit video data (e.g., the signal VID) and/or the converted data determined based on the computer vision operations (e.g., the signal META) to the communication device 114. In still another example, the interface may be configured to transmit directional audio output (e.g., the signal DIR_AOUT) to each of the speakers 122a-122n. The interface may be configured to enable transfer of data and/or translate data from one format to another format to ensure that the data transferred is readable by the intended destination component. In an example, the interface may comprise a data bus, traces, connectors, wires and/or pins. The implementation of the interface may be varied according to the design criteria of a particular implementation.

The signal VID may be presented to the communication device 114. In some embodiments, the signal VID may be an encoded, cropped, stitched and/or enhanced version of one or more of the signals FRAMES_A-FRAMES_N (e.g., the captured video frames). In an example, the signal VID may be a high resolution, digital, encoded, de-warped, stabilized, cropped, blended, stitched and/or rolling shutter effect corrected version of the signals FRAMES_A-FRAMES_N.

The signal META may be presented to the communication device 114. In some embodiments, the signal META may be a text message (e.g., a string of human readable characters). In some embodiments, the signal META may be a symbol that indicates an event or status (e.g., a fire symbol indicating a fire has been detected, a heart symbol indicating a health issue has been detected, a symbol of a person walking to indicate that one of the subjects 62a-62b has left the field of view 102a-102n, etc.). The signal META may be generated based on video analytics (e.g., computer vision operations) performed by the processor 116 on the video frames FRAMES_A-FRAMES_N. The processor 116 may be configured to perform the computer vision operations to detect objects and/or events in the video frames FRAMES_A-FRAMES_N and then convert. The data determined by the computer vision operations may be converted to the human-readable format by the processor 116. The data from the computer vision operations that has been converted to the human-readable format may be communicated as the signal META.

In some embodiments, the signal META may be data generated by the processor 116 (e.g., video analysis results, speech analysis results, profile information of users, etc.) that may be communicated to a cloud computing service in order to aggregate information and/or provide training data for machine learning (e.g., to improve speech recognition, to improve facial recognition, to provide relevant ads to the users, etc.). The type of information communicated by the signal META may be varied according to the design criteria of a particular implementation.

In an example, a cloud computing platform (e.g., distributed computing such as the network 72) may be implemented as a group of cloud-based, scalable server computers. By implementing a number of scalable servers, additional resources (e.g., power, processing capability, memory, etc.) may be available to process and/or store variable amounts of data. For example, the cloud computing service may be configured to scale (e.g., provision resources) based on demand. The scalable computing may be available as a service to allow access to processing and/or storage resources without having to build infrastructure (e.g., the provider of the apparatus 100 may not have to build the infrastructure of the cloud computing service).

In some embodiments, the processor 116 may be further configured to forward audio commands received to a cloud computing service via the communication device 114. The cloud computing service may determine the instruction provided by the subjects 62a-62n, the cloud computer service may communicate the instruction(s) to the processor 116 via the communication device 114 and the processor 116 may perform the instruction(s). In some embodiments, the processor 116 may generate instructions determined by the processor 116 that are sent using the communication device 114 to an external component in order to be performed. In an example, if the audio command is to purchase a product, the processor 116 may determine the instructions from the audio 80, generate instruction signals in response to the product purchase instruction (e.g., comprising information about the product to be purchased). The communication device 114 may communicate with a shopping service (e.g., in a format compatible with an API for an online store) and the shopping service may be the external component that fulfills the purchase of the product.

The apparatus 100 may implement a camera system. In some embodiments, the camera system 100 may be implemented as a drop-in solution (e.g., installed as one component). In an example, the camera system 100 may be a device that may be installed as an after-market product (e.g., a retro-fit for a drone, a retro-fit for a security system, etc.). In some embodiments, the apparatus 100 may be a component of a security system. The number and/or types of signals and/or components implemented by the camera system 100 may be varied according to the design criteria of a particular implementation.

The video data of the targeted view captured in the field of view 102a-102b may be represented as the signals/bitstreams/data FRAMES_A-FRAMES_N (e.g., video signals). The capture devices 112a-112n may present the signals FRAMES_A-FRAMES_N to the inputs 130a-130n of the processor 116. The signals FRAMES_A-FRAMES_N may represent the video frames/video data. The signals FRAMES_A-FRAMES_N may be video streams captured by the capture devices 112a-112n. In some embodiments, the capture devices 112a-112n may be implemented in the camera system 100. In some embodiments, the capture devices 112a-112n may be configured to add to existing functionality to the camera system 100.

Each of the capture devices 112a-112n may comprise a block (or circuit) 140, a block (or circuit) 142, and/or a block (or circuit) 144. The circuit 140 may implement a camera sensor (e.g., a complementary metal-oxide-semiconductor (CMOS) sensor). The circuit 142 may implement a camera processor/logic. The circuit 144 may implement a memory buffer. As a representative example, the capture device 112a is shown comprising the sensor 140a, the logic block 142a and the buffer 144a. The camera sensors 140a-140n may receive light from the corresponding one of the lenses 110a-110n and transform the light into digital data (e.g., the bitstreams).

In one example, the sensor 140a of the capture device 112a may receive light from the lens 110a. The camera sensor 140a of the capture device 112a may perform a photoelectric conversion of the light from the lens 110a. In some embodiments, the sensor 140a may be an oversampled binary image sensor. The logic 142a may transform the bitstream into a human-legible content (e.g., video data). For example, the logic 142a may receive pure (e.g., raw) data from the camera sensor 140a and generate video data based on the raw data (e.g., the bitstream). The memory buffer 144a may store the raw data and/or the processed bitstream. For example, the frame memory and/or buffer 144a may store (e.g., provide temporary storage and/or cache) one or more of the video frames (e.g., the video signal).

The microphones 120a-120n may be configured to capture incoming audio and/or provide directional information about the incoming audio. Each of the microphones 120a-120n may receive a respective signal (e.g., AIN_A-AIN_N). The signals AIN_A-AIN_N may be audio signals from the environment near the apparatus 100. For example, the signals AIN_A-AIN_N may be ambient noise in the environment and/or the audio 80 from the subjects 62a-62n. The microphones 120a-120n may be configured to generate the signal DIR_AUD in response to the signals AIN_A-AIN_N. The signal DIR_AUD may be a signal that comprises the audio data from the signals AIN_A-AIN_N. The signal DIR_AUD may be a signal generated in a format that provides directional information about the signals AIN_A-AIN_N.

The microphones 120a-120n may provide the signal DIR_AUD to the interface 136. The apparatus 100 may comprise the interface 136 configured to receive data (e.g., the signal DIR_AUD) from one or more of the microphones 120a-120n. In one example, data from the signal DIR_AUD presented to the interface 136 may be used by the processor 116 to determine the location of the source of the audio 80. In another example, the microphones 120a-120n may be configured to determine the location of the audio 80 and present the location to the interface 136 as the signal DIR_AUD.

The number of microphones 120a-120n may be varied according to the design criteria of a particular implementation. The number of microphones 120a-120n may be selected to provide sufficient directional information about the incoming audio (e.g., the number of microphones 120a-120n implemented may be varied based on the accuracy and/or resolution of directional information acquired). In an example, 2 to 6 of the microphones 120a-120n may be implemented. In some embodiments, an audio processing component may be implemented with the microphones 120a-120n to process and/or encode the incoming audio signals AIN_A-AIN_N. In some embodiments, the processor 116 may be configured with on-chip audio processing. The microphones 120a-120n may capture audio of the environment. The apparatus 100 may be configured to synchronize the audio captured with the images captured by the capture devices 112a-112n.

The processor 116 may be configured to execute computer readable code and/or process information. The processor 116 may be configured to receive input and/or present output to the memory 118. The processor 116 may be configured to present and/or receive other signals (not shown). The number and/or types of inputs and/or outputs of the processor 116 may be varied according to the design criteria of a particular implementation.

The processor 116 may receive the signals FRAMES_A-FRAMES_N, the signal DIR_AUDIO and/or the signal DATA. The processor 116 may make a decision based on data received at the inputs 130a-130n, the input 132, the input 136 and/or other input. For example other inputs may comprise external signals generated in response to user input, external signals generated by the microphones 120a-120n and/or internally generated signals such as signals generated by the processor 116 in response to analysis of the signals FRAMES_A-FRAMES_N and/or objects detected in the signals FRAMES_A-FRAMES_N. The processor 116 may adjust the video data (e.g., crop, digitally move, physically move the camera sensor 140, etc.) of the signals FRAMES_A-FRAMES_N. The processor 116 may generate the signal VID, the signal META and/or the signal DIR_AOUT in response data received by the inputs 130a-130n, the input 132, the input 136 and/or the decisions made in response to the data received by the inputs 130a-130n, the input 132 and/or the input 136.

The signal VID, the signal META and/or the signal DIR_AOUT may be generated to provide an output in response to the captured video frames (e.g., the signal FRAMES_A-FRAMES_N) and the video analytics performed by the processor 116. For example, the video analytics may be performed by the processor 116 in real-time and/or near real-time (e.g., with minimal delay). In one example, the signal VID may be a live (or nearly live) video stream.

Generally, the facial recognition video operations performed by the processor 116 may correspond to the data received at the inputs 130a-130n, the input 132, the input 136 and/or enhanced (e.g., stabilized, corrected, cropped, downscaled, packetized, compressed, etc.) by the processor 116. For example, the facial recognition video operations may be performed in response to a stitched, corrected, stabilized, cropped and/or encoded version of the signals FRAMES_A-FRAMES_N. The processor 116 may further encode and/or compress the signals FRAMES_A-FRAMES_N to generate the signal COMM.

The cropping, downscaling, blending, stabilization, packetization, encoding, compression and/or conversion performed by the processor 116 may be varied according to the design criteria of a particular implementation. For example, the signal VID may be a processed version of the signals FRAMES_A-FRAMES_N configured to fit the target area to the shape and/or specifications of a playback device (e.g., the remote devices 54a-54n). For example, the remote devices 54a-54n may be implemented for real-time video streaming of the signal VID received from the apparatus 100.

In some embodiments, the signal VID may be some view (or derivative of some view) captured by the capture devices 112a-112n. For example, the signal VID may comprise a portion of the panoramic video captured by the capture devices 112a-112n. In another example, the signal VID may be a video frame comprising the region of interest selected and/or cropped from the panoramic video frame by the processor 116. The signal VID may comprise a video frame having a smaller size than the panoramic video frames FRAMES_A-FRAMES_N. In some embodiments, the signal VID may provide a series of cropped and/or enhanced panoramic video frames that improve upon the view from the perspective of the camera system 100 (e.g., provides night vision, provides High Dynamic Range (HDR) imaging, provides more viewing area, highlights detected objects, provides additional data such as a numerical distance to detected objects, provides visual indicators for paths of a race course, etc.).

The memory 118 may store data. The memory 118 may be implemented as a cache, flash memory, DRAM memory, etc. The type and/or size of the memory 118 may be varied according to the design criteria of a particular implementation. The data stored in the memory 118 may correspond to a video file, a facial recognition database, user profiles, user permissions, etc.

The lenses 110a-110n (e.g., camera lenses) may be directed to provide a panoramic view from the camera system 100. The lenses 110a-110n may be aimed to capture environmental data (e.g., light). The lens 110a-110n may be configured to capture and/or focus the light for the capture devices 112a-112n. Generally, the camera sensor 140 is located behind each of the lenses 110a-110n. Based on the captured light from the lenses 110a-110n, the capture devices 112a-112n may generate a bitstream and/or video data.

Embodiments of the processor 116 may perform video stitching operations on the signals FRAMES_A-FRAMES_N. In one example, each of the video signals FRAMES_A-FRAMES_N may provide a portion of a panoramic view and the processor 116 may crop, blend, synchronize and/or align the signals FRAMES_A-FRAMES_N to generate the panoramic video frames. In some embodiments, the processor 116 may be configured to perform electronic image stabilization (EIS). The processor 116 may perform de-warping on the signals FRAMES_A-FRAMES_N. The processor 116 may perform intelligent video analytics on the de-warped video frames FRAMES_A-FRAMES_N. The processor 116 may encode the signals FRAMES_A-FRAMES_N to a particular format.

In some embodiments, the cropped and/or enhanced portion of the panoramic video generated by the processor 116 may be sent to the output 134a (e.g., the signal VID). In one example, the signal VID may be an HDMI output. In another example, the signal VID may be a composite (e.g., NTSC) output (e.g., composite output may be a low-cost alternative to HDMI output). In yet another example, the signal VID may be a S-Video output. In some embodiments, the signal VID may be an output sent via interfaces such as USB, SDIO, Ethernet and/or PCIe. The portion of the panoramic video signal VID may be output to the wireless communication device 114.

The video generated by the processor 116 may also be used to implement a panoramic video having high-quality video in the region of interest. The video generated by the processor 116 may be used to implement a panoramic video that reduces bandwidth needed for transmission by cropping out the portion of the panoramic that has not been selected by the intelligent video analytics and/or the directional audio signal DIR_AUD as the region of interest. To generate a high-quality, enhanced video using the region of interest, the processor 116 may be configured to perform encoding, blending, cropping, aligning and/or stitching.

The encoded video may be processed locally and discarded, stored locally and/or transmitted wirelessly to external storage and/or external processing (e.g., network attached storage, cloud storage, distributed processing, etc.). In one example, the encoded, panoramic video may be stored locally by the memory 118. In another example, the encoded, panoramic video may be stored to a hard-drive of a networked computing device. In yet another example, the encoded, panoramic video may be transmitted wirelessly without storage. The type of storage implemented may be varied according to the design criteria of a particular implementation.

In some embodiments, the processor 116 may be configured to send analog and/or digital video out (e.g., the signal VID) to the video communication device 114. In some embodiments, the signal VID generated by the apparatus 100 may be a composite and/or HDMI output. The processor 116 may receive an input for the video signal (e.g., the signals FRAMES_A-FRAMES_N) from the CMOS sensor(s) 140a-140n. The input video signals FRAMES_A-FRAMES_N may be enhanced by the processor 116 (e.g., color conversion, noise filtering, auto exposure, auto white balance, auto focus, etc.).

Generally, the panoramic video may comprise a large field of view generated by one or more lenses/camera sensors. One example of a panoramic video may be an equirectangular 360 video. Equirectangular 360 video may also be called spherical panoramas. Panoramic video may be a video that provides a field of view that is larger than the field of view that may be displayed on a device used to playback the video. For example, the field of view 102a-102b captured by the camera system 100 may be used to generate panoramic video such as a spherical video, a hemispherical video, a 360 degree video, a wide angle video, a video having less than a 360 field of view, etc.

Panoramic videos may comprise a view of the environment near the camera system 100. In one example, the entire field of view 102a-102b of the panoramic video may be captured at generally the same time (e.g., each portion of the panoramic video represents the view from the camera system 100 at one particular moment in time). In some embodiments (e.g., when the camera system 100 implements a rolling shutter sensor), a small amount of time difference may be present between some portions of the panoramic video. Generally, each video frame of the panoramic video comprises one exposure of the sensor (or the multiple sensors 140a-140n) capturing the environment near the camera system 100.

In some embodiments, the field of view 102a-102b may provide coverage for a full 360 degree field of view. In some embodiments, less than a 360 degree view may be captured by the camera system 100 (e.g., a 270 degree field of view, a 180 degree field of view, etc.). In some embodiments, the panoramic video may comprise a spherical field of view (e.g., capture video above and below the camera system 100). For example, the camera system 100 may be mounted on a ceiling and capture a spherical field of view of the area below the camera system 100. In some embodiments, the panoramic video may comprise a field of view that is less than a spherical field of view (e.g., the camera system 100 may be configured to capture the ground below and the areas to the sides of the camera system 100 but nothing directly above). The implementation of the camera system 100 and/or the captured field of view 102a-102b may be varied according to the design criteria of a particular implementation.

In embodiments implementing multiple lenses, each of the lenses 110a-110n may be directed towards one particular direction to provide coverage for a full 360 degree field of view. In embodiments implementing a single wide angle lens (e.g., the lens 110a), the lens 110a may be located to provide coverage for the full 360 degree field of view (e.g., on the bottom of the camera system 100 in a ceiling mounted embodiment, on the bottom of a drone camera, etc.). In some embodiments, less than a 360 degree view may be captured by the lenses 110a-110n (e.g., a 270 degree field of view, a 180 degree field of view, etc.). In some embodiments, the lenses 110a-110n may move (e.g., the direction of the capture devices may be controllable). In some embodiments, one or more of the lenses 110a-110n may be configured to implement an optical zoom (e.g., the lenses 110a-110n may zoom in/out independent of each other).

In some embodiments, the apparatus 100 may be implemented as a system on chip (SoC). For example, the apparatus 100 may be implemented as a printed circuit board comprising one or more components (e.g., the capture devices 112a-112n, the processor 116, the communication device 114, the memory 118, etc.). The apparatus 100 may be configured to perform intelligent video analysis on the video frames of the de-warped, panoramic video. The apparatus 100 may be configured to crop and/or enhance the panoramic video.

In some embodiments, the processor 116 may be configured to perform sensor fusion operations. The sensor fusion operations performed by the processor 116 may be configured to analyze information from multiple sources (e.g., the capture devices 112a-112n and the microphones 120a-120n). By analyzing various data from disparate sources, the sensor fusion operations may be capable of making inferences about the data that may not be possible from one of the data sources alone. For example, the sensor fusion operations implemented by the processor 116 may analyze video data (e.g., mouth movements of the subjects 62a-62n) as well as the speech patterns from the directional audio DIR_AUD. The disparate sources may be used to develop a model of a scenario to support decision making. For example, the processor 116 may be configured to compare the synchronization of the detected speech patterns with the mouth movements in the video frames to determine which person in a video frame is speaking. The sensor fusion operations may also provide time correlation, spatial correlation and/or reliability among the data being received.

In some embodiments, the processor 116 may implement convolutional neural network capabilities. The convolutional neural network capabilities may implement computer vision using deep learning techniques. The convolutional neural network capabilities may be configured to implement pattern and/or image recognition using a training process through multiple layers of feature-detection.

The signal DIR_AOUT may be an audio output. For example, the processor 116 may generate output audio based on information extracted from the video frames FRAMES_A-FRAMES_N. The signal DIR_AOUT may be determined based on an event and/or objects determined using the computer vision operations. In one example, the signal DIR_AOUT may comprise an audio message asking the subjects 62a-62n for permission to stream the signal VID. In some embodiments, the signal DIR_AOUT may not be generated until an event has been detected by the processor 116 using the computer vision operations.

The signal DIR_AOUT may comprise directional and/or positional audio output information for the speakers 122a-122n. The speakers 122a-122n may receive the signal DIR_AOUT, process the directional and/or positional information and determine which speakers and/or which channels will play back particular audio portions of the signal DIR_AOUT. The speakers 122a-122n may generate the signals AOUT_A-AOUT_N in response to the signal DIR_AOUT. The signals AOUT_A-AOUT_N may be the audio message played to the subjects 62a-62n. For example, the speakers 122a-122n may emit a pre-recorded message in response to a detected event. The signal DIR_AOUT may be a signal generated in a format that provides directional information for the signals AOUT_A-AOUT_N.

The number of speakers 122a-122n may be varied according to the design criteria of a particular implementation. The number of speakers 122a-122n may be selected to provide sufficient directional channels for the outgoing audio (e.g., the number of speakers 122a-122n implemented may be varied based on the accuracy and/or resolution of directional audio output). In an example, 1 to 6 of the speakers 122a-122n may be implemented. In some embodiments, an audio processing component may be implemented by the speakers 122a-122n to process and/or decode the output audio signals DIR_AOUT. In some embodiments, the processor 116 may be configured with on-chip audio processing. In some embodiments, the signal DIR_AOUT may playback audio received from the remote devices 54a-54n in order to implement a 2-way real-time audio communication.

Figure 4:
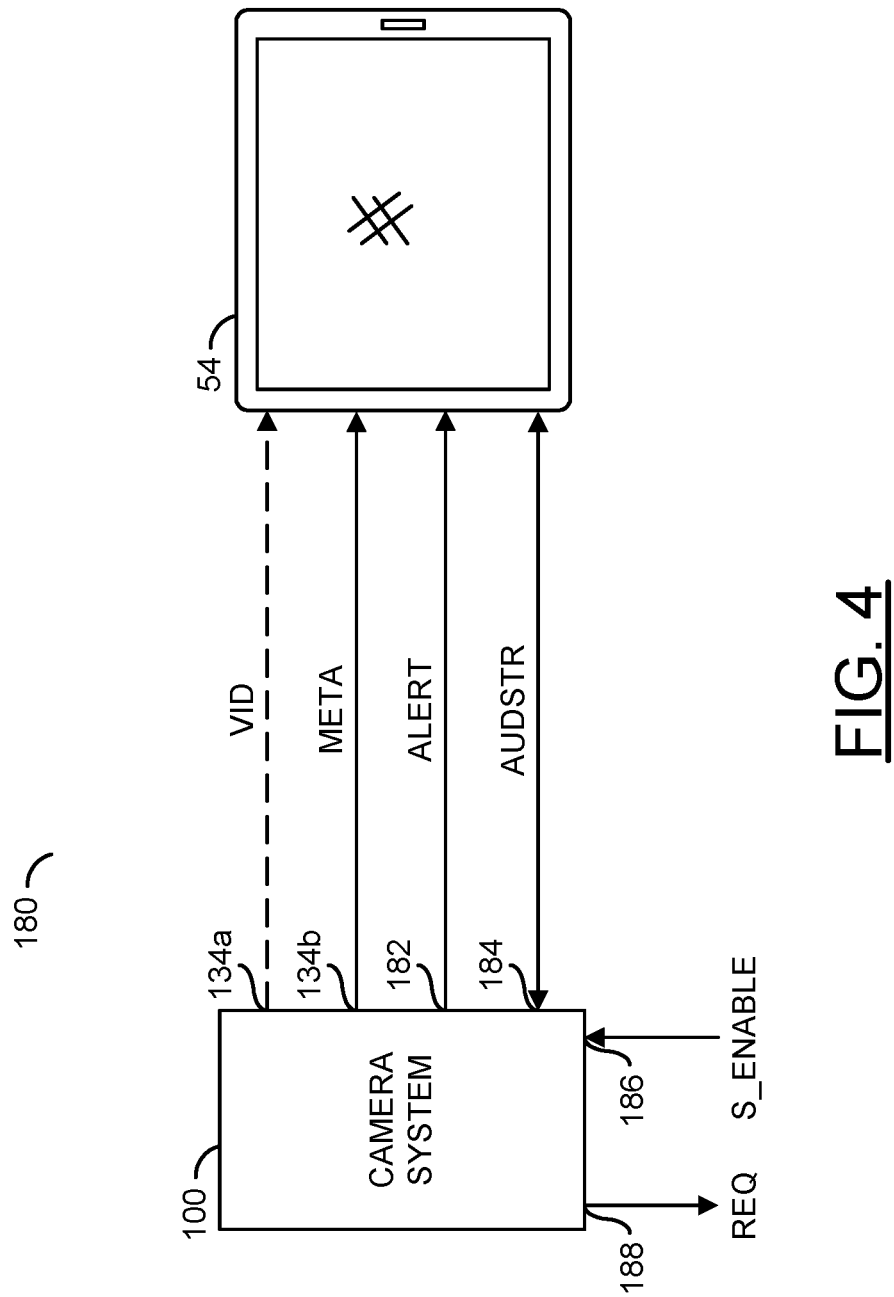
FIG. 4 is a diagram illustrating communication between a camera system and a remote device.

Referring to FIG. 4, a diagram illustrating communication between the camera system 100 and the remote device 54 is shown. A system 180 is shown comprising the camera system 100 and the remote device 54. The camera system 100 may be a representative example of the camera systems 100a-100n. The remote device 54 may be a representative example of the remote devices 54a-54n. The camera system 100 is shown comprising the outputs 134a-134b, an output 182, an input/output 184, an input 186 and/or an output 188. In some embodiments, the outputs 134a-134b, the output 182 and/or the input/output 184 may be communication (e.g., wireless) by the communication device 114. The input 186 may be received by one or more of the directional microphones 120a-120n. The output 188 may be presented by the speakers 122a-122n. The number and/or types of inputs and/or outputs of the camera system 100 may be varied according to the design criteria of a particular implementation.

The output 134a may present the signal VID to the remote device 54. The output 134b may present the signal META to the remote device 54. The output 182 may present a signal (e.g., ALERT). The input/output 184 may send/receive a signal (e.g., AUDSTR). While the signal VID, the signal META the signal ALERT and the signal AUDSTR may be shown communicated directly between the camera system 100 and the remote device 54, the signals may be communicated via the network 72 shown in association with FIG. 2.

The input 186 may receive a signal (e.g., S_ENABLE). The output 188 may present a signal (e.g., REQ). The signal S_ENABLE may be received from an audio source (e.g., one of the subjects 62a-62n). The signal REQ may be presented to one or more of the subjects 62a-62n.

The signal ALERT may be a notification sent to the remote device 54. The signal ALERT may be generated in response to an emergency event. The emergency event may be based on the computer vision analysis performed by the processor 116. The emergency event may be an event that is determined to warrant an immediate response from one of the patient monitors 52a-52n. For example, if the event detected by the computer vision operations is a cardiac arrest, the signal ALERT may be generated.

The signal AUDSTR may communicate audio data for two-way audio communication. For example, the directional microphones 120a-120n may capture audio from one or more of the subjects 62a-62n and the signal AUDSTR may stream the audio to the remote device 54. A speaker implemented by or connected to the remote device 54 may playback the streamed audio to the patient monitors 52a-52n. Similarly, a microphone implemented by or connected to the remote device 54 may capture audio from one or more of the patient monitors 52a-52n and the signal AUDSTR may stream the audio to the camera system 100. The speakers 122a-122n may playback the streamed audio to the subjects 62a-62n. While the signal AUDSTR is shown as a bi-directional signal, the 2-way audio communication may be implemented over separate channels.

The signal REQ may be an audio output of the capture device 100. For example, the signal REQ may represent one or more of the output signals AOUT_A-AOUT_N shown in association with FIG. 3. The signal REQ may be a request for permission to stream the video data. In an example, the signal REQ may be a pre-recorded message (e.g., "May I have permission to stream video to your doctor?"). In another example, the signal REQ may be a procedurally generated message (e.g., audio generated based on speech patterns and language rules for asking a specific question that is not pre-recorded). In some embodiments, the signal REQ may be generated in response to the computer vision operations implemented by the processor 116 detecting an event.

The signal S_ENABLE may represent the audio 80 captured by the camera system 100. In one example, the signal S_ENABLE may be the permission to stream the video data to the remote device 54. For example, the signal REQ may ask for permission to stream the video data and the user may respond with the signal S_ENABLE to provide permission to stream the video data. For example, the signal S_ENABLE may be an affirmative response to a question provided by the signal REQ. The signal S_ENABLE may be a verbal command detected in the captured audio. For example, the permission status to stream the video data may be determined in response to verbal commands detected.

In the example system 180, the signal VID is shown as a dashed line. The signal VID may not be generated and/or communicated to the remote device 54 unless one or more of the subjects 62a-62n provides permission. In an example, the processor 116 may monitor the subjects 62a-62n using the computer vision operations. When the computer vision operations detect an event, the camera system 100 may generate the signal REQ to ask the subjects 62a-62n for permission to stream the video data. If the subjects 62a-62n do not provide permission (e.g., the signal S_ENABLE is not received), the signal VID may not be communicated to the remote device 54. If permission is received (e.g., the signal S_ENABLE is received and provides an affirmative response for permission), the signal VID may be streamed from the camera system 100 to the remote device 54.

The camera system 100 may be configured to record video data (e.g., store locally in the memory 118). The camera system 100 may be configured to stream (e.g., communicate to another device and/or location) the video data. The camera system 100 may be configured to record and stream video data simultaneously. Generally, permission from the subjects 62a-62n may not be needed to record the video data. Generally, permission from the subjects 62a-62n may be needed to stream the video data.

The memory 118 may be configured to store the recorded video data and/or store the captured audio. In some embodiments, the recorded video data may be used as reference and/or training data to improve object analysis and/or classification using computer vision processing. In some embodiments, the video data and/or the captured audio may be stored by the memory 118 for evidential purposes. For example, the memory 118 may store the audio 80 that has been determined to grant permission to stream the video data (e.g., as proof that permission was granted). In another example, the recorded video data and/or the captured audio may be stored as part of a medical record.

In some embodiments, the permission status may have granular permissions. For example, the permission status may grant permission to stream the video data to the remote devices 54a-54n but not allow storage of the streamed video data. In another example, the permission status may grant permission to stream the video data to the remote devices 54a-54n but deny permission to store the video data in the cloud services 72. In yet another example, the permission status may grant permission to stream the video data to the remote devices 54a-54n and grant permission to allow the video data to be stored by the cloud services 72. The granularity of the permission status may be varied according to the design criteria of a particular implementation.

Figure 5:
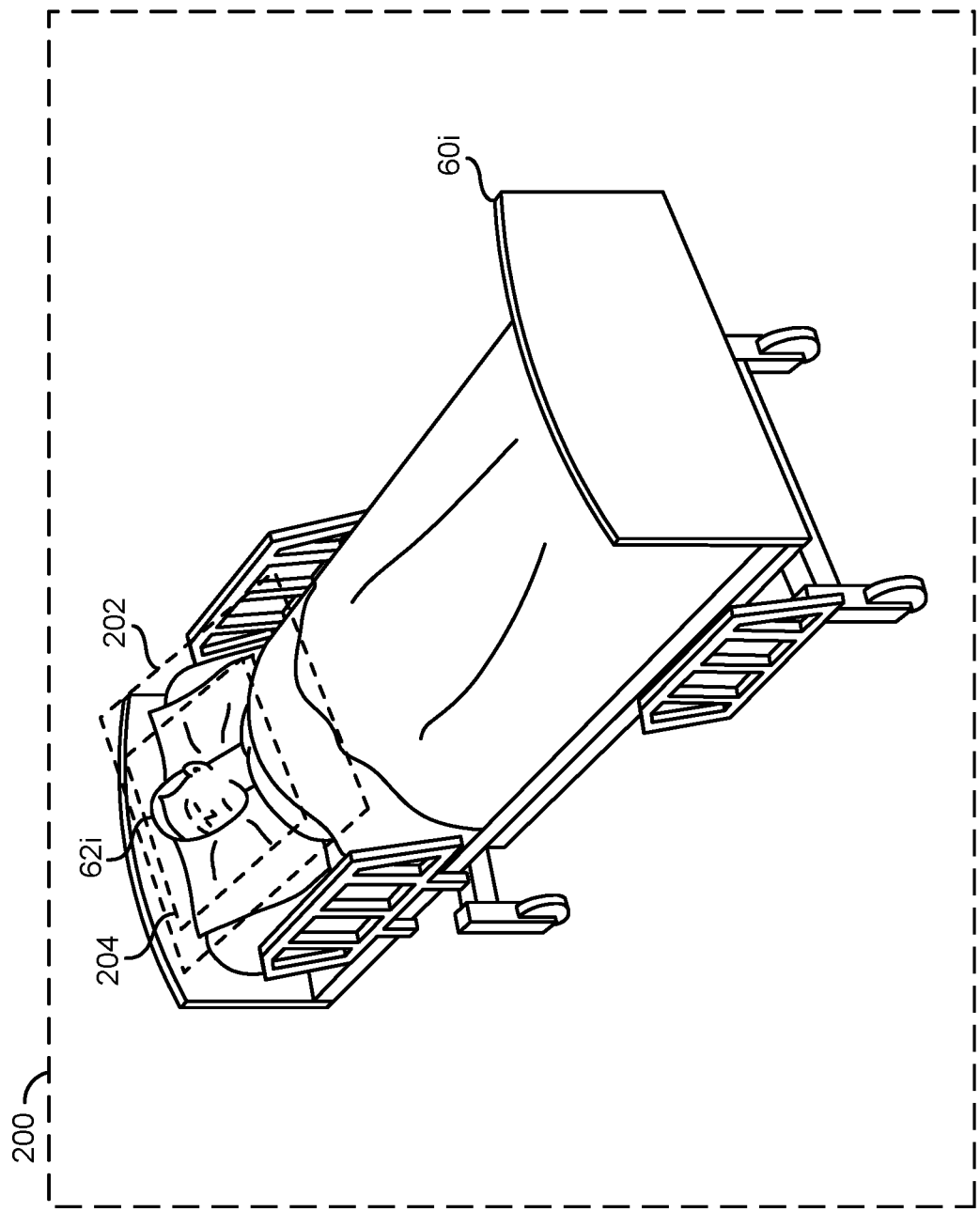
FIG. 5 is a diagram illustrating monitoring a patient in an example video frame.

Referring to FIG. 5, a diagram illustrating monitoring a patient in an example video frame 200 is shown. The example video frame 200 may be an example of one type of scenario for monitoring the subjects 62a-62n (e.g., a patient monitoring scenario). The patient 62i is shown lying down in the bed 60i in the example video frame 200. The example video frame 200 may be one of the video frames FRAMES_A-FRAMES_N. In the example shown, the camera systems 100a-100n may implement patient monitoring cameras using computer vision and audio assistance to maintain the privacy of the patient 62i.

A box 202 and a box 204 are shown in the example video frame 200. The box 202 and the box 204 may represent detections, classifications and/or inferences made by the computer vision operations implemented by the processor 116. The box 202 may represent an object detection determined by video operations performed by the processor 116. The object detection 202 may be detecting the subject 62i. The box 204 may represent a detection of a characteristic and/or an event performed by the processor 116. In the example video frame 200, one object detection 202 and one characteristic 204 are shown. However, the number of objects detected and/or the number and/or types of characteristics of each object detected may be varied according to the design criteria of a particular implementation.

In the example video frame 200, the subject 62i may be detected as the object 202. In one example, the characteristics 204 of the object 202 may be that the subject 62i is lying down (e.g., sleeping peacefully) in the bed 60i. In another example, the characteristics 204 may identify the subject 62i as a particular person based on facial recognition operations performed by the processor 116. Generally, a patient sleeping may not be an event. Since no event has been detected, the camera system 100 may not send the signal ALERT to the remote device 54. Since no event has been detected, the camera system 100 may not generate the signal REQ to ask for permission to stream the video. For example, the processor 116 may analyze the information (e.g., characteristics of the objects) detected in the video frames in order to make inferences about what is happening.

The processor 116 may then determine whether what has been inferred is an event that may be worth streaming to the patient monitors 52a-52n. Whether an event is worth streaming may be determined based on pre-defined rules. The pre-defined rules may be adjusted by the patient monitors 52a-52n, vendors of the processor 116, firmware providers for the processor 116, etc. For example, if there is no event detected, the camera systems 100a-100n may maintain the privacy of the patient 62i by not streaming video data (e.g., streaming video may invade the current amount of privacy of the patient 62i).

In some embodiments, the processor 116 may convert the detected characteristics 204 into the human readable format. For example, the processor 116 may detect the characteristics 204 as the subject 62i sleeping in the bed 60i. The processor 116 may convert the characteristics 204 to a human readable format. In one example, the processor 116 may convert the detected characteristics to a short message (e.g., a text message reading, "the patient is currently sleeping"). In another example, the processor 116 may convert the detected characteristics 204 to a symbol that represents the detected characteristics 204 (e.g., to indicate that the subject 62i is sleeping, an icon of ZZZ may be presented). The characteristics 204 converted to the human readable format may be communicated as the signal META to the remote device 54. The signal META may provide the patient monitors 52a-52n an indication of a status of the subjects 62a-62n with less invasion of privacy than streaming the video signal VID.

Figure 6:
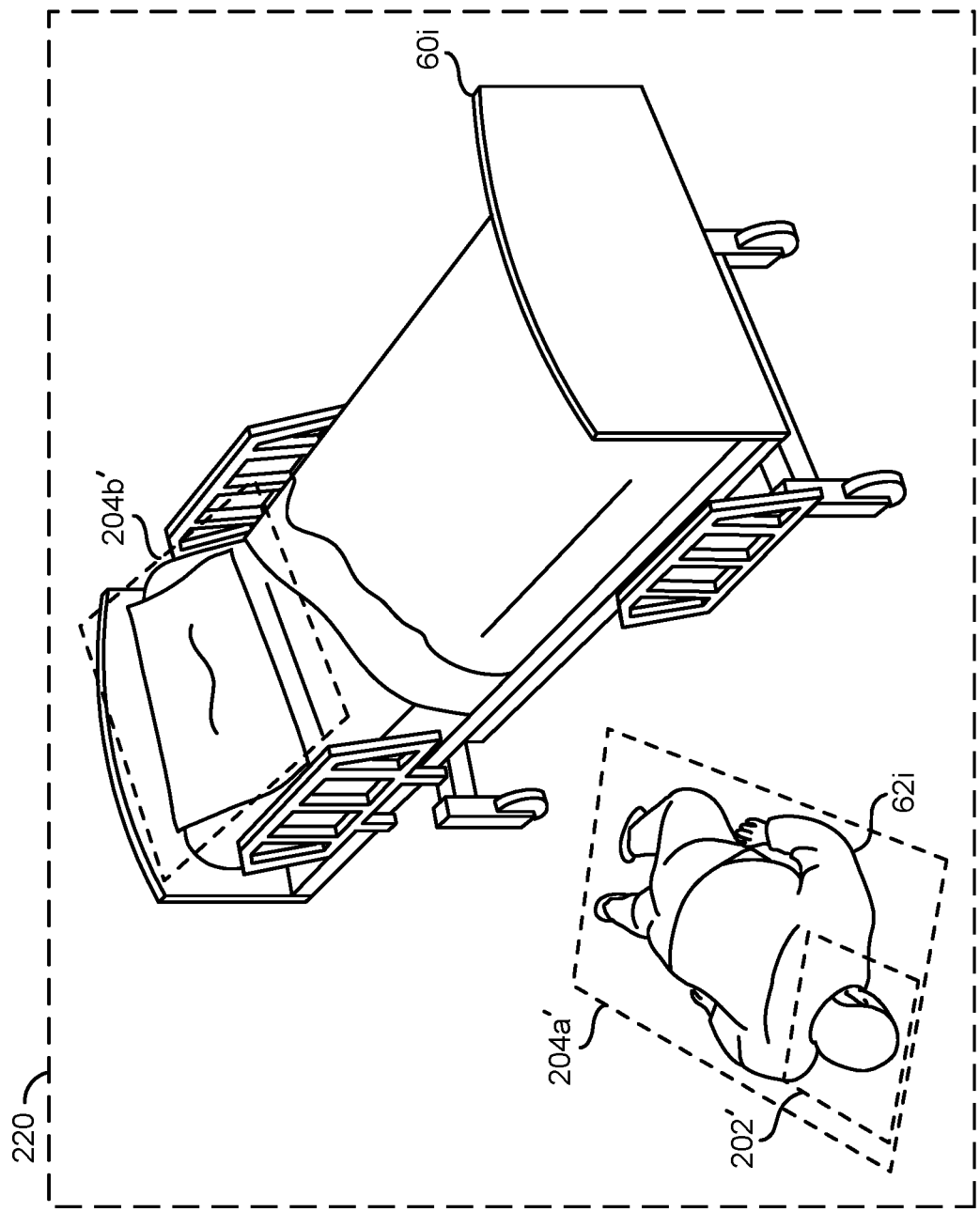
FIG. 6 is a diagram illustrating detecting an event in a patient monitoring embodiment.

Referring to FIG. 6, a diagram illustrating detecting an event in a patient monitoring embodiment is shown. An example video frame 220 may be an example of one type event for one type of scenario for monitoring the subjects 62a-62n (e.g., a patient monitoring scenario). The patient 62i is shown lying on the floor beside the bed 60i in the example video frame 220 (e.g., fallen out of bed). The example video frame 220 may be one of the video frames FRAMES_A-FRAMES_N. For example, the example video frame 220 may be a video frame captured after the example video frame 200 shown in association with FIG. 5.

The box 202' and the boxes 204a'-204b' are shown in the example video frame 220. The box 202' and the boxes 204a'-204b' may represent detections, classifications and/or inferences made by the computer vision operations implemented by the processor 116. The box 202' may represent an object detection performed by the processor 116. The object detection 202' may be detecting the subject 62i. The boxes 204a'-204b' may each represent a detection of a characteristic and/or a detection of an event performed by the processor 116. The detected characteristics 204a' may correspond to the subject 62i and the detected characteristics 204b' may correspond to the bed 60i.

In the example video frame 220, the subject 62i may be detected as the object 202'. The characteristics 204a' of the object 202' may be that the subject 62i is lying down on the floor beside the bed 60i. The characteristics 204b' of the bed 60i may be that the bed 60i is empty. Generally, a patient lying down may not be an event (e.g., a patient lying down may be sleeping as shown in association with FIG. 5). However, the processor 116 may be configured to make inferences based on multiple characteristics 204a'-204b' to come to a conclusion that may not be detected from one source of information alone. For example, the characteristic of lying down 204a' may not be an event. But a combination of the characteristic of lying down 204a' and the characteristic 204b' of the bed 60i being empty may lead to an inference that the subject 62i has fallen down and may need medical attention (e.g., the characteristics 204a'-204b' may be an event). The processor 116 may infer from the detected object 202' and/or the characteristics 204a'-204b' that an event has occurred.

In response to the detected event, the processor 116 may generate the signal REQ and/or the signal ALERT. In an example, if the event is determined to be urgent (e.g., additional characteristics such as bleeding and/or body parts being bent the wrong way may indicate a serious injury) the signal ALERT may be generated. Generally, after the event has been detected, the processor 116 may monitor the captured audio from the microphones 120a-120n in order to determine whether the permission status allows the video stream (e.g., the processor 116 may check the captured audio for the signal S_ENABLE).

The signal REQ may be generated to ask the subject 62*i* for permission to stream the video data. The camera system 100 may monitor audio (e.g., the signal DIR_AUD presented by the microphones 120*a*-120*n*) in response to the event in order to determine the permission status of the subject 62*i*. If the subject 62*i* does not grant permission to stream the video data, the processor 116 may not present the signal VID to the remote devices 54*a*-54*n*. If the subject 62*i* grants permission to stream the video data, the processor 116 may generate the signal VID. In some embodiments, if the subject 62*i* is unresponsive then permission to stream may be inferred (e.g., unresponsive may be determined based on the characteristics to distinguish between sleeping normally and potential medical issues).

Figure 7:
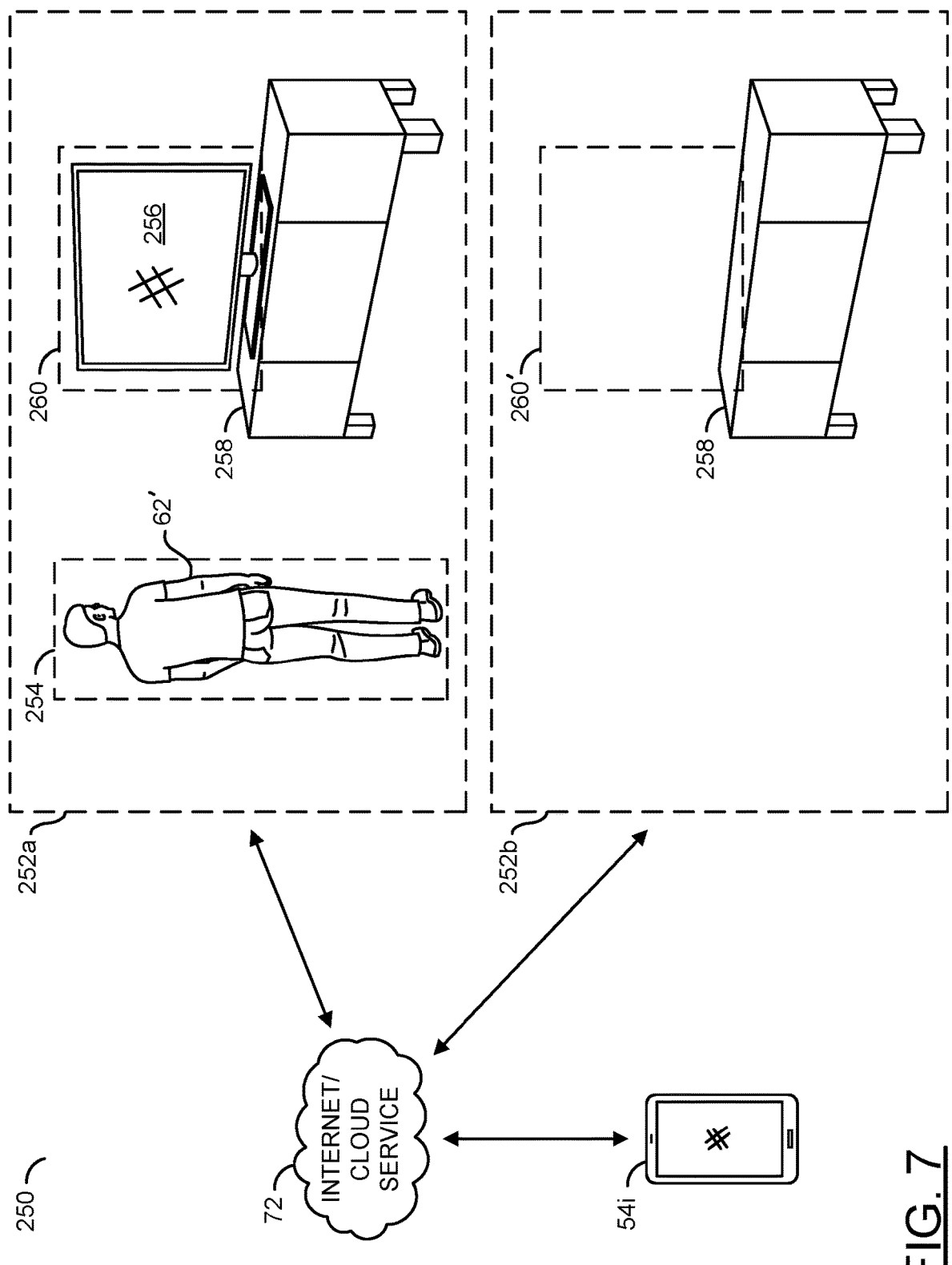
FIG. 7 is a diagram illustrating example video frames in a rental property embodiment.

Referring to FIG. 7, a diagram illustrating example video frames in a rental property embodiment 250 is shown. The example embodiment 250 may represent an alternate use case for the camera systems 100*a*-100*n*. For example, the alternate use case may be an AirBnB rental and the camera systems 100*a*-100*n* may monitor the presence of the renter without compromising privacy. The example scenario 250 may comprise the remote device 54*i*, the network 72 and/or example video frames 252*a*-252*b*.

The example video frames 252*a*-252*b* may be an example of one type of event for one type of scenario for monitoring the subjects 62*a*-62*n* (e.g., a rental property scenario). The example video frames 252*a*-252*b* may each be one of the video frames FRAMES_A-FRAMES_N. In the example shown, the example video frame 252*b* may be a video frame captured after the example video frame 252*a*. The example video frames 252*a*-252*b* may be captured by one of the camera systems 100*a*-100*n* and communicated to the network 72.

In the example video frame 252*a*, a subject 62' is shown. The subject 62' may be a person renting the property. A box 254 is shown. The box 254 may represent the object detection performed by the processor 116. For example, the computer vision operations may detect the object 254 as the subject 62'.

In some embodiments, the presence of the object 254 may be the event. For example, the owner of the property may want to know when the renter 62' arrives (e.g., to provide a courtesy welcome phone call, or provide instructions, or to make sure the renter 62' is satisfied with the accommodations). In response to the event being detected, the camera system 100 may present the signal REQ with the audio message asking for permission to stream video. If the renter 62' declines to give permission, the camera system 100 may not generate the signal VID.

In the example video frame 252*a*, a TV 256 is shown on top of a stand 258. A box 260 is shown. The box 260 may represent the object detection performed by the processor 116. For example, the computer vision operations may detect the object 260 as the TV 256 located on the stand 258. In some embodiments, the camera system 100 may be configured to track the location of the detected objects.

In the example video frame 252*b*, the TV 256 is not shown on top of the stand 258. A box 260' is shown. The box 260' may represent the characteristics of the object detected by the processor 116. For example, the computer vision operations may detect that the characteristics 260' of the object 260 is that the object is missing by comparing the characteristics of the TV 256 from one frame (e.g., not missing in the video frame 252*a*) to another video frame (e.g., missing in the video frame 252*b*). For example, an object that is missing and/or a damaged object may be an event detected by the processor 116.

In some embodiments, in response to the event of the missing TV 260', the camera system 100 may generate the signal REQ to ask for permission from the renter 62' to stream the video. In some embodiments, terms of the rental agreement may indicate that damage or potential theft of objects may give implicit permission to stream the video data. For example, the missing TV event 260' may provide the permission for generating the signal VID without the signal S_ENABLE as a response from the renter 62'.

In some embodiments, the cloud service 72 may be configured to store the video frames generated by the camera systems 100*a*-100*n*. For example, the signal VID may be presented to the cloud services 72 for storage but not streamed to the remote device 54*i* without permission. Storing the video data to the cloud service 72 may enable the monitors 52*a*-52*n* to review previously captured video data in response to the event. In one example, a routine surgery may not have permission to stream the video data, but if an event is detected (e.g., the patient bleeds out) the video data may be reviewed later for investigative purposes (e.g., to determine what caused the bleed). In another example, the video data of the renter 62' may not have permission to stream the video data to the remote device 54*i*', but once the theft event 260' is detected, the property owner may have permission to review the video data stored in the cloud service 72 to determine if the renter 62' stole the TV 256.

Figure 8:
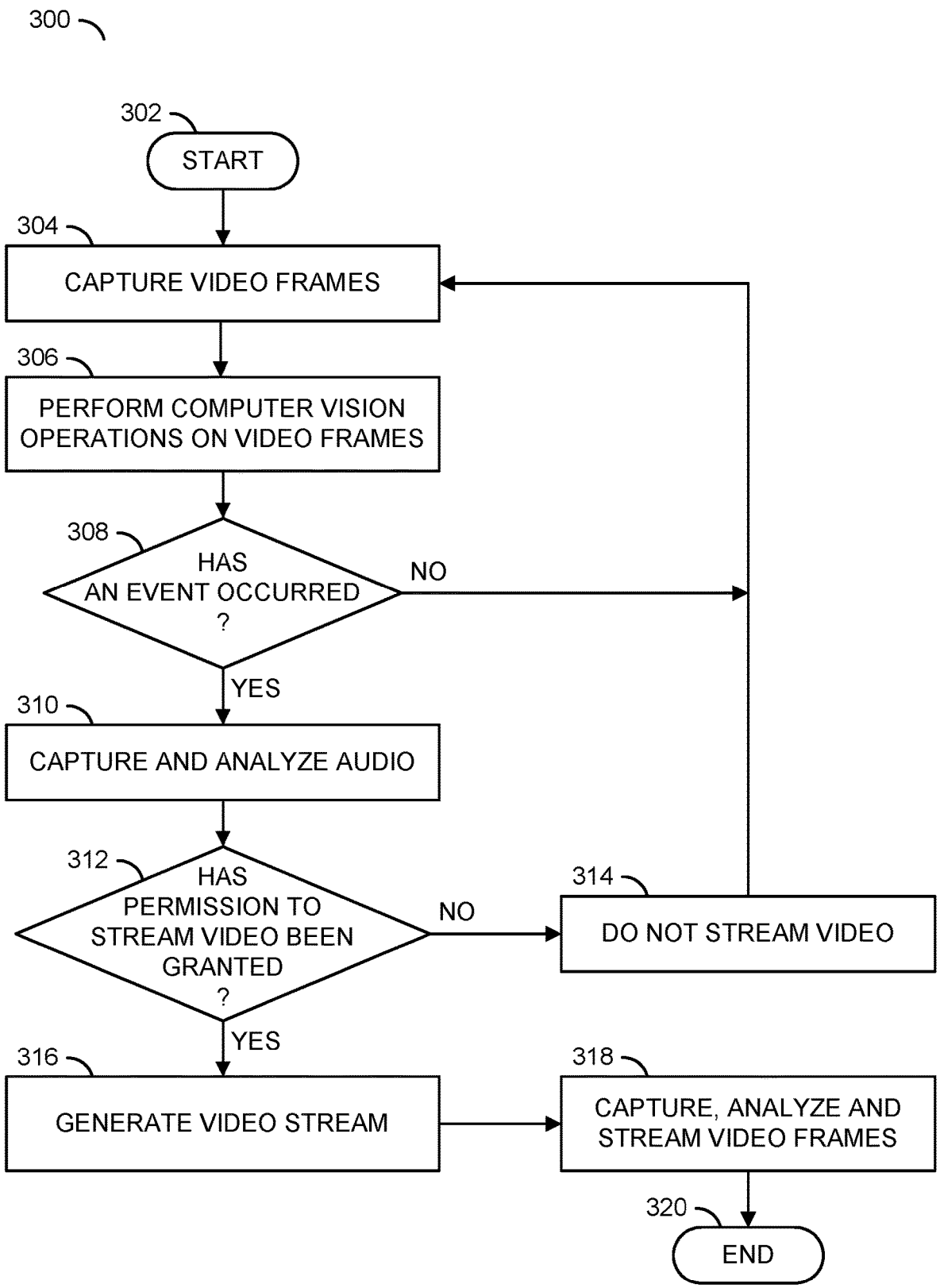
FIG. 8 is a flow diagram illustrating a method for performing video operations on captured video frames to determine a permission status.

Referring to FIG. 8, a method (or process) 300 is shown. The method 300 may perform video operations on captured video frames to determine a permission status. The method 300 generally comprises a step (or state) 302, a step (or state) 304, a step (or state) 306, a decision step (or state) 308, a step (or state) 310, a decision step (or state) 312, a step (or state) 314, a step (or state) 316, a step (or state) 318, and a step (or state) 320.

The step 302 may start the method 300. In the step 304, the capture devices 112*a*-112*n* may capture the video frames and present the video frames FRAMES_A-FRAMES_N to the processor 116. In the step 306, the processor 116 may perform the computer vision operations on the video frames FRAMES_A-FRAMES_N. Next, the method 300 may move to the decision step 308.

In the decision step 308, the processor 116 may determine whether an event has occurred. The event may be detected by performing the computer vision operations on the video frames and analyzing the objects 202 and/or the characteristics 204 of the objects to determine whether a pattern has been detected that corresponds to an event. If the event has not occurred, the method 300 may return to the step 304. If the event has occurred, the method 300 may move to the step 310. In the step 310, the microphones 120*a*-120*n* may capture the audio input AIN_A-AIN_N and present the directional audio DIR_AUD to the processor 116 and the processor 116 may analyze the directional audio (e.g., perform intelligent audio processing to determine a permission status). Next, the method 300 may move to the decision step 312.

In the decision step 312, the processor 116 may determine whether permission has been granted to stream the video. In an example, the captured audio (e.g., verbal commands) may be analyzed for speech patterns and/or keywords that may be recognized as providing permission to stream the video. If permission has not been granted, the method 300 may move to the step 314. In the step 314, the camera system 100 may not stream the video data. Next, the method 300 may return to the step 304.

In the decision step 312, if the permission has been granted, the method 300 may move to the step 316. In the step 316, the processor 116 may generate the video stream VID. For example, the video stream VID may be presented to the communication device 114 and communicated to one or more of the remote devices 54a-54n. Next, in the step 318, the camera system 100 may capture, analyze and stream video frames. Next, the method 300 may move to the step 320. The step 320 may end the method 300.

Figure 9:
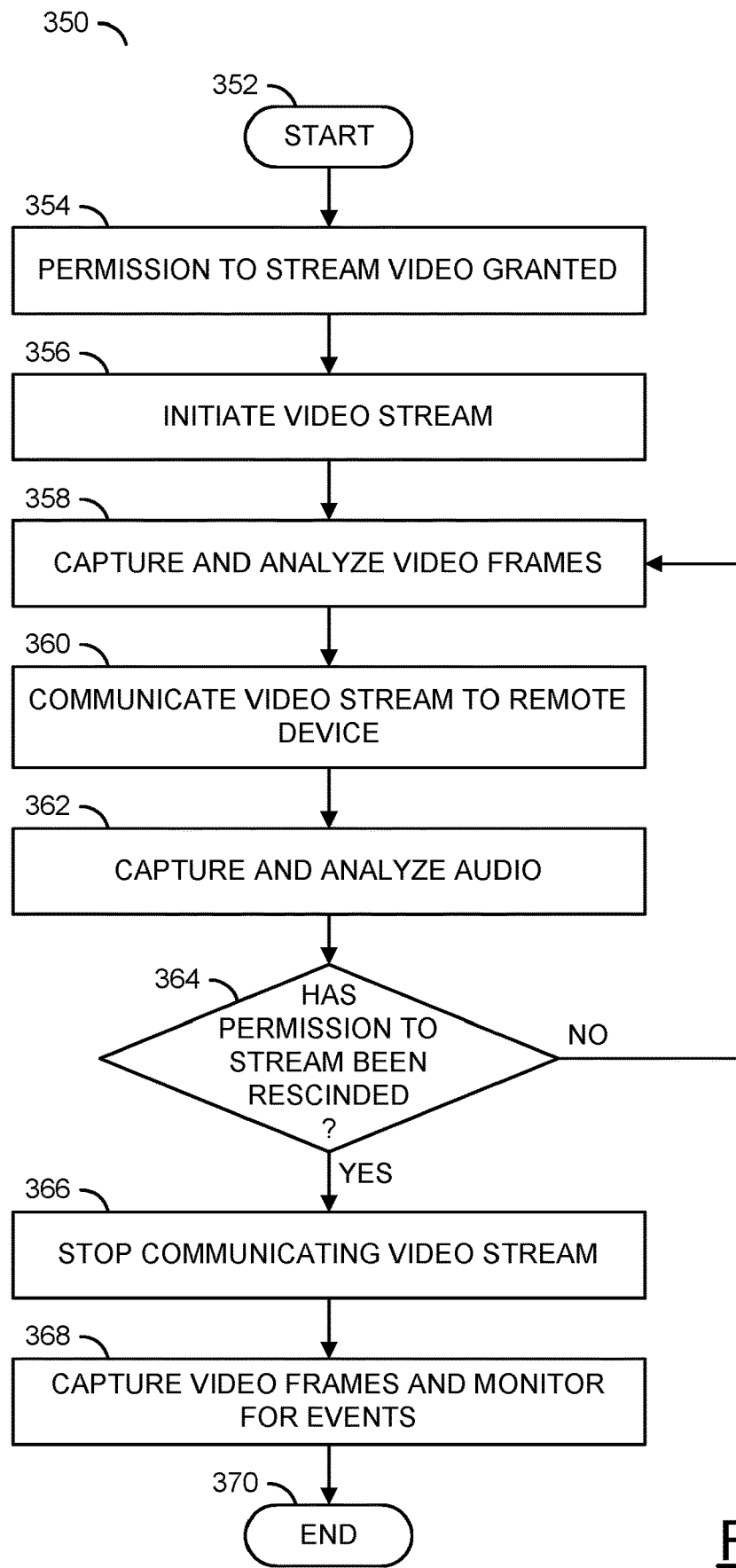
FIG. 9 is a flow diagram illustrating a method for stopping a video stream when permission is rescinded.

Referring to FIG. 9, a method (or process) 350 is shown. The method 350 may stop a video stream when permission is rescinded. The method 350 generally comprises a step (or state) 352, a step (or state) 354, a step (or state) 356, a step (or state) 358, a step (or state) 360, a step (or state) 362, a decision step (or state) 364, a step (or state) 366, a step (or state) 368, and a step (or state) 370.

The step 352 may start the method 350. In the step 354, the processor 116 may determine that the permission to stream has been granted (e.g., based on the intelligent audio processing performed on the captured audio). For example, the signal S_ENABLE may have been received. In another example, the audio 80 may have been received and analyzed and the processor 116 may have determined that the audio speech pattern comprises a granting of permission by the subjects 62a-62n. Next, in the step 356, the processor 116 may initiate the video stream VID. In the step 358, the processor 116 may capture and analyze the video frames FRAMES_A-FRAMES_N. Next, in the step 360, the communication device 114 may communicate the video stream. VID to the remote devices 54a-54n. In the step 362, the microphones 120a-120n may capture the audio AIN_A-AIN_N, present the directional audio DIR_AUD to the processor 116 and the processor 116 may analyze the audio. In some embodiments, the steps 356-362 may be performed substantially in parallel. Next, the method 350 may move to the decision step 364.

In the decision step 364, the processor 116 may determine whether permission to stream the video data has been rescinded. For example, the subjects 62a-62n may have previously granted permission then later decided that streaming the video is no longer desired. The processor 116 may analyze the audio and recognize speech to determine whether the speech indicates that permission is no longer granted (e.g., a change in the permission status that denies allowing the video stream). If the permission has not been rescinded, the method 350 may return to the step 358. If the permission has been rescinded, the method 350 may move to the step 366.

In the step 366, the processor 116 and/or the communication device 114 may stop communicating the video stream VID. Next, in the step 368, the camera system 100 may capture the video frames and monitor the video frames for events using the computer vision analysis. Next, the method 350 may move to the step 370. The step 370 may end the method 350.

Figure 10:
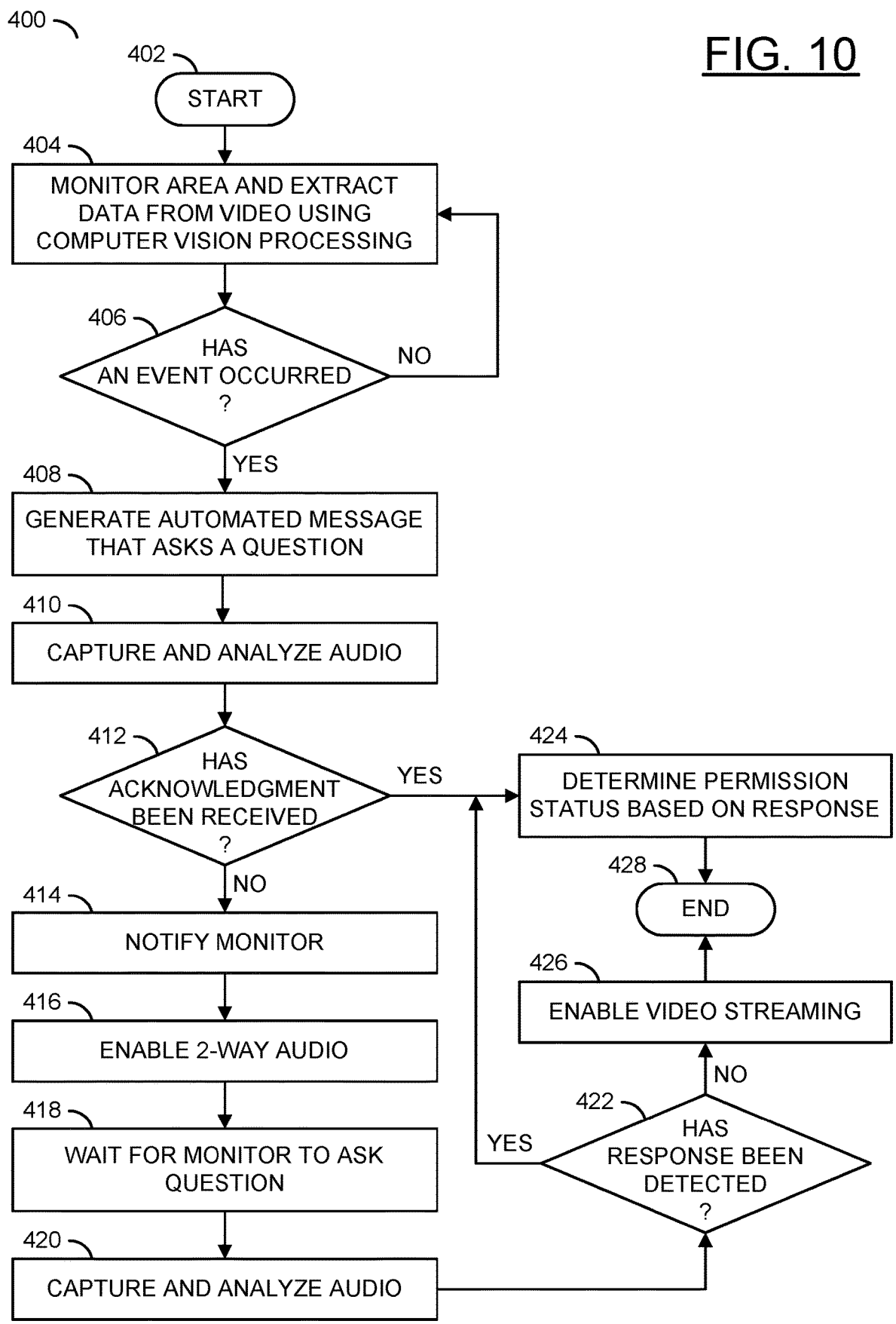
FIG. 10 is a flow diagram illustrating a method for enabling 2-way communication to determine a permission status.

Referring to FIG. 10, a method (or process) 400 is shown. The method 400 may enable 2-way communication to determine a permission status. The method 400 generally comprises a step (or state) 402, a step (or state) 404, a decision step (or state) 406, a step (or state) 408, a step (or state) 410, a decision step (or state) 412, a step (or state) 414, a step (or state) 416, a step (or state) 418, a step (or state) 420, a decision step (or state) 422, a step (or state) 424, a step (or state) 426, and a step (or state) 428.

The step 402 may start the method 400. In the step 404, the processor 116 may monitor the area (e.g., the locations 70a-70n) and extract data from the video using computer vision processing. Next, the method 400 may move to the decision step 406.

In the decision step 406, the processor 116 may determine whether an event has occurred. For example, the event may be that no motion has been detected (e.g., the patient has not moved in a long time), the patient has left a pre-defined area (e.g., not visible in the video frames and/or moved to a restricted area), the patient is lying down but not in bed (e.g., fallen out of bed and onto the floor) and/or other behavioral warning signs (e.g., signs of distress such as clutching at the chest, bleeding, flailing, convulsing, etc.). If the event has not occurred, the method 400 may return to the step 404. If the processor 116 determines that an event has occurred, the method 400 may move to the step 408.

In the step 408, the processor 116 may generate an automated message that asks a question (e.g., the signal DIR_AOUT) and the speakers 122a-122n may present the audio signals AOUT_A-AOUT_N to the subjects 62a-62n. In one example, the automated message may ask a patient, "Are you okay?". Next, in the step 410, the microphones 120a-120n may capture the audio AIN_A-AIN_N and present the directional audio DIR_AUD to the processor 116 and the processor 116 may analyze the audio. Next, the method 400 may move to the decision step 412.

In the decision step 412, the processor 116 may determine whether acknowledgment has been received from the subjects 62a-62n. The processor 116 may perform intelligent audio processing. For example, the processor 116 may analyze the captured audio DIR_AUD for speech patterns and determine whether the speech patterns generally match an anticipated response to the question. For example, if the automated message asks whether the patient is okay, an anticipated response may be "yes" or "no". If acknowledgment has been received, the method 400 may move to the step 424. If acknowledgment has not been received, the method 400 may move to the step 414.

In the step 414, the processor 116 may generate the signal META and the communication device 114 may communicate the signal META to the remote devices 54a-54n. For example, the signal META may comprise a message for the patient monitors 52a-52n that comprises a notification that an event has been detected and that one or more of the patients 62a-62n have not responded. Next, in the step 416, the camera system 100 may enable the 2-way audio. In an example, the communication device 114 may communicate the signal AUDSTR between the camera system 100 and the remote device 54. For example, the microphones 120a-120n may capture audio and the communication device 114 may communicate the captured audio to the remote device 54. Similarly, the remote device 54 may communicate captured audio from the patient monitors 52a-52n and the speakers 122a-122n may playback the audio received to the subjects 62a-62n. Next, in the step 418, the camera system 100 may wait for the patient monitors 52a-52n to ask a question. In the step 420, the microphones 120a-120n may capture the audio signals AIN_A-AIN_N and the present the directional audio signal DIR_AUD to the processor 116 and the processor 116 may analyze the audio for a response from the subjects 62a-62n. Next, the method 400 may move to the decision step 422.

In the decision step 422, the processor 116 may determine whether a response has been detected. If a response has been detected, the method 400 may move to the step 424. In the step 424, the processor 116 may determine the permission status based on the response received. For example, if the automated message and/or the patient monitor has asked, "Are you okay" and the patient has responded "yes" there may not be a reason to stream the video (e.g., the privacy of the patient may have a higher priority). In another example, if the automated message and/or the patient monitor has asked, "Are you okay" and the patient has responded "I'm hurt" then there may be implicit permission to stream the video (e.g., the patient safety may have a higher priority than the patient privacy). In some embodiments, the permission status may be based on a terms of service agreement that defines particular situations (e.g., events and/or responses by the patient) that may assume that permission to stream video has been granted. Next, the method 400 may move to the step 428.

In the decision step 422, if no response has been detected, the method 400 may move to the step 426. In the step 426, the processor 116 may enable streaming of the video signal VID. For example, if there is no response, an assumption may be made that the patient is in danger and the patient monitor 52a-52n should be able to see what is happening. Next, the method 400 may move to the step 428. The step 428 may end the method 400.

Figure 11:
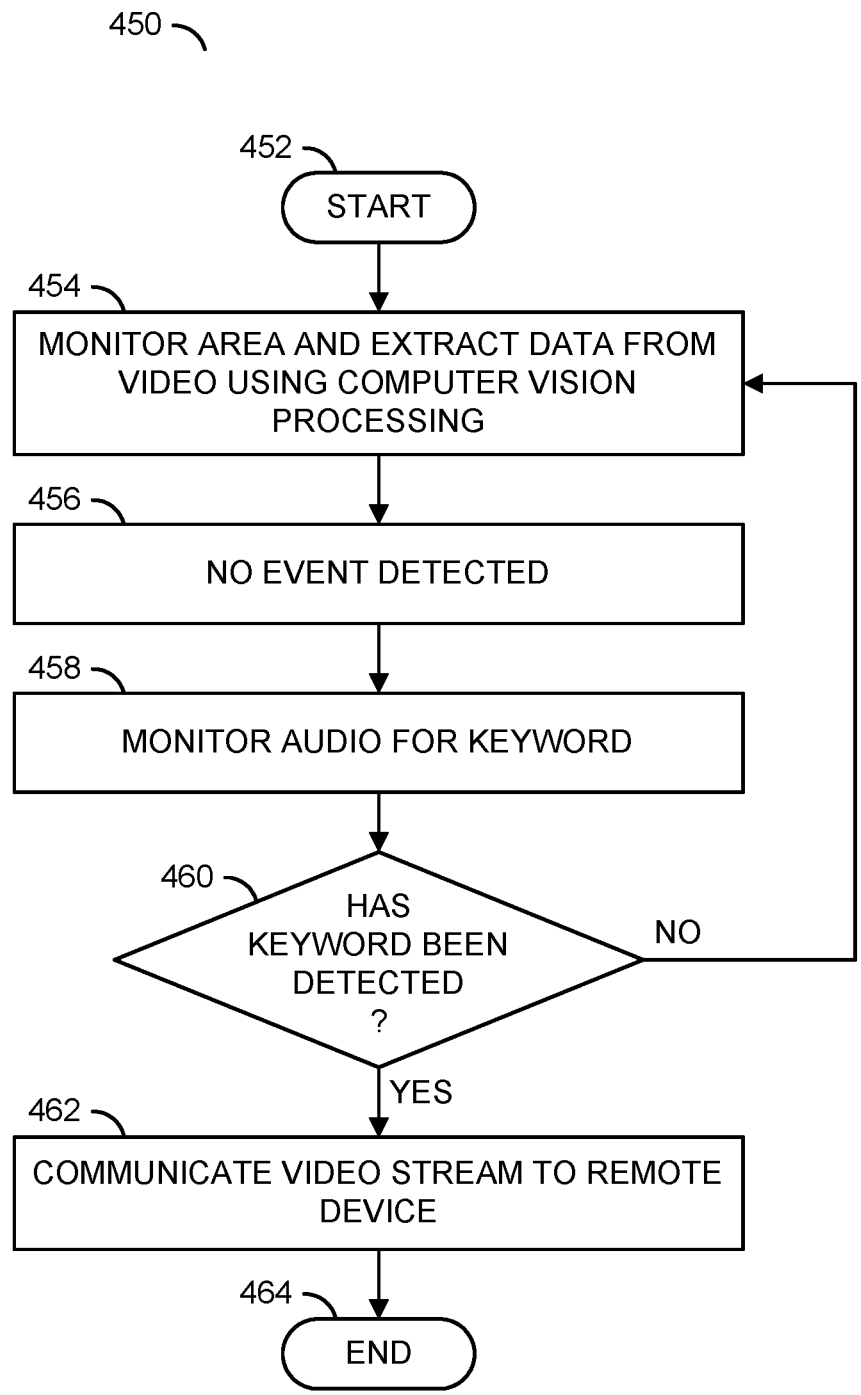
FIG. 11 is a flow diagram illustrating a method for enabling a video stream in response to detecting a keyword.

Referring to FIG. 11, a method (or process) 450 is shown. The method 450 may enable a video stream in response to detecting a keyword. The method 450 generally comprises a step (or state) 452, a step (or state) 454, a step (or state) 456, a step (or state) 458, a decision step (or state) 460, a step (or state) 462, and a step (or state) 464.

The step 452 may start the method 450. In the step 454, the processor 116 may monitor the area (e.g., the locations 70a-70n) and extract data from the video using computer vision processing. Next, in the step 456, the processor 116 may determine that, based on the computer vision processing, no event has been detected. In the step 458, the processor 116 may monitor the captured audio using intelligent audio processing for a keyword. In an example, the keyword may be a pre-defined audio pattern that is used to enable video streaming (e.g., "start streaming"). For example, the microphones 120a-120n may capture the audio AIN_A-AIN_N and present the directional audio DIR_AUD to the processor 116 and the processor 116 may analyze the directional audio for speech patterns. Next, the method 450 may move to the decision step 460.

In the decision step 460, the processor 116 may determine whether the keyword has been detected. If the keyword has not been detected, the method 450 may return to the step 454. If the keyword has been detected, the method 450 may move to the step 462. Next, in the step 462, the processor 116 may present the signal VID to the communication device 114 to stream the video data to the remote devices 54a-54n. In an example, the keyword may enable the subjects 62a-62n to activate video streaming without having the processor 116 first detect an event. Next, the method 450 may move to the step 464. The step 464 may end the method 450.

Figure 12:
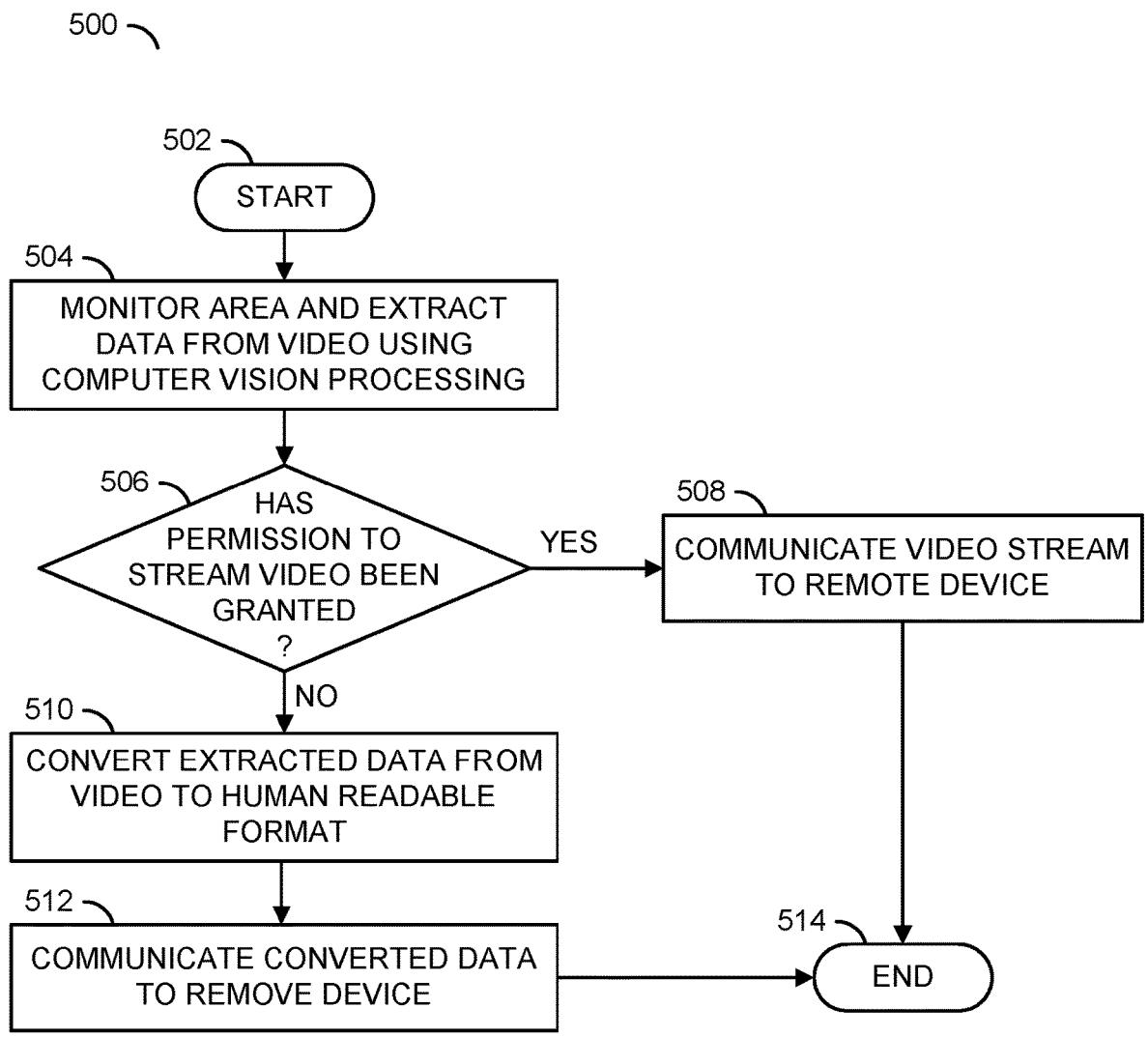
FIG. 12 is a flow diagram illustrating a method for converting events detected in the video data to a human readable format.

Referring to FIG. 12, a method (or process) 500 is shown. The method 500 may convert events detected in the video data to a human readable format. The method 500 generally comprises a step (or state) 502, a step (or state) 504, a decision step (or state) 506, a step (or state) 508, a step (or state) 510, a step (or state) 512, and a step (or state) 514.

The step 502 may start the method 500. In the step 504, the processor 116 may monitor the area (e.g., the locations 70a-70n) and extract data from the video using computer vision processing. Next, the method 500 may move to the decision step 506.

In the decision step 506, the processor 116 may determine whether permission to stream the video data has been granted. If the permission has been granted, the method 500 may move to the step 508. In the step 508, the processor 116 may communicate the signal VID to the remote devices 54a-54n via the communication device 114. Next, the method 500 may move to the step 514.

In the decision step 506, if the permission to stream the video data has not been granted, the method 500 may move to the step 510. In the step 510, the processor 116 may convert the video data extracted from the video frames FRAMES_A-FRAMES_N to a human readable format (e.g., text, icons, etc.). Next, in the step 512, the processor 116 may communicate the converted data as the signal META (e.g., a notification) to the remote devices 54a-54n via the communication device 114. Next, the method 500 may move to the step 514. The step 514 may end the method 500.

The functions performed by the diagrams of FIGS. 1-12 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the specification, as will be apparent to those skilled in the relevant art(s). Appropriate software, firmware, coding, routines, instructions, opcodes, microcode, and/or program modules may readily be prepared by skilled programmers based on the teachings of the disclosure, as will also be apparent to those skilled in the relevant art(s). The software is generally executed from a medium or several media by one or more of the processors of the machine implementation.

The invention may also be implemented by the preparation of ASICs (application specific integrated circuits), Platform ASICs, FPGAs (field programmable gate arrays), PLDs (programmable logic devices), CPLDs (complex programmable logic devices), sea-of-gates, RFICs (radio frequency integrated circuits), ASSPs (application specific standard products), one or more monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The invention thus may also include a computer product which may be a storage medium or media and/or a transmission medium or media including instructions which may be used to program a machine to perform one or more processes or methods in accordance with the invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMs (random access memories), EPROMs (erasable programmable ROMs), EEPROMs (electrically erasable programmable ROMs), UVPROMs (ultra-violet erasable programmable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, cloud servers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, audio storage and/or audio playback devices, video recording, video storage and/or video playback devices, game platforms, peripherals and/or multi-chip modules. Those skilled in the relevant art(s) would understand that the elements of the invention may be implemented in other types of devices to meet the criteria of a particular application.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

While the invention has been particularly shown and described with reference to embodiments thereof, it will be understood by those skilled in the art that various changes in form and details may be made without departing from the scope of the invention.

The invention claimed is:

1. An apparatus comprising:
   a video capture device configured to generate a plurality of video frames of a person being monitored, said video frames stored internally to said apparatus;
   an audio capture device configured to capture audio of said person being monitored; and
   a processor configured to
   (i) perform video operations to detect one or more objects in said video frames stored internally to said apparatus,
   (ii) extract data about said one or more objects based on characteristics of said one or more objects determined using said video operations,
   (iii) detect whether an event relating to said person being monitored has occurred based on (a) said characteristics of said objects and (b) behavioral warning signs of said person being monitored detected in said video operations indicating said person needs attention,
   (iv) perform an analysis of said captured audio of said person being monitored after said event has been detected,
   (v) determine a permission status provided by said person being monitored based on said captured audio received from said person being monitored currently by said video operations, and
   (vi) generate a video stream internally to said apparatus based on said video frames,
   wherein said video stream is transmitted from said apparatus only if said permission status provided by said person being monitored allows transmission of said video stream.

2. The apparatus according to claim 1, wherein said apparatus is configured to implement a patient monitoring camera using computer vision and audio assistance to maintain privacy of said person.

3. The apparatus according to claim 1, wherein (i) said apparatus further comprises a communication device and (ii) said communication device is configured to communicate said video stream to a remote device.

4. The apparatus according to claim 3, wherein said remote device comprises at least one of a tablet computing device, a smartphone or a patient monitor.

5. The apparatus according to claim 1, wherein said video stream enables monitoring said person being monitored from a remote geographic location.

6. The apparatus according to claim 1, wherein said permission status is determined in response to verbal commands detected in said captured audio after said event has been detected using said video operations.

7. The apparatus according to claim 1, wherein (i) said video capture device comprises a wide angle lens and (ii) a field of view of said wide angle lens captures panoramic video frames.

8. The apparatus according to claim 1, wherein said audio capture device comprises one or more directional microphones configured to provide information corresponding to a direction of a source of said audio.

9. The apparatus according to claim 1, wherein said characteristics of said event comprise at least one of (a) no motion detected by said person being monitored, (b) one of said objects has left a pre-defined area, or (c) said person being monitored has fallen out of bed.

10. The apparatus according to claim 1, wherein (i) said apparatus further comprises an audio output device and (ii) said audio output device is configured to emit a pre-recorded message in response to said event.

11. The apparatus according to claim 10, wherein said permission status is determined by monitoring said captured audio received in response to said pre-recorded message using audio processing to parse speech commands from the captured audio.

12. The apparatus according to claim 10, wherein a notification is provided to a remote device if no response is received in response to said pre-recorded message.

13. The apparatus according to claim 12, wherein (i) said apparatus is further configured to implement two-way audio communication with said remote device and (ii) and said permission status is determined in response to said two-way audio communication.

14. The apparatus according to claim 1, wherein said captured audio is analyzed for a keyword to provide said permission status when said event has not been detected.

15. The apparatus according to claim 1, wherein (i) a transfer of said video stream from said apparatus is started in response to said permission status and (ii) said transfer of said video stream from said apparatus is stopped after a change of said permission status is detected that denies allowing said video stream from said apparatus.

16. The apparatus according to claim 1, wherein (i) said data about said objects extracted using said video operations is converted to a human readable format and (ii) said human readable format is communicated to a remote device when said permission status does not allow said video stream.

17. The apparatus according to claim 1, wherein (i) said apparatus is one of a plurality of apparatuses and (ii) said apparatuses enable remote monitoring of a plurality of people from at least one remote device.

* * * * *